United States Patent
Camras et al.

(10) Patent No.: US 10,369,050 B2
(45) Date of Patent: Aug. 6, 2019

(54) DEVICE AND METHOD FOR REDUCING INTRAOCULAR PRESSURE

(71) Applicant: Camras Vision Inc., Research Triangle Park, NC (US)

(72) Inventors: Lucinda J. Camras, Durham, NC (US); Rand Allingham, Durham, NC (US); Bruce Klitzman, Durham, NC (US); Sanjay Asrani, Chapel Hill, NC (US)

(73) Assignee: Camras Vision Inc., Research Triangle Park, NC (US)

( * ) Notice: Subject to any disclaimer, the term of this patent is extended or adjusted under 35 U.S.C. 154(b) by 0 days.

(21) Appl. No.: 16/043,099

(22) Filed: Jul. 23, 2018

(65) Prior Publication Data
US 2018/0325733 A1   Nov. 15, 2018

Related U.S. Application Data

(63) Continuation of application No. 14/473,228, filed on Aug. 29, 2014, now Pat. No. 10,201,451.

(51) Int. Cl.
  *A61F 9/007* (2006.01)
(52) U.S. Cl.
  CPC .. *A61F 9/00781* (2013.01); *A61F 2250/0024* (2013.01); *A61F 2250/0051* (2013.01)
(58) Field of Classification Search
  CPC .............. A61F 9/00781; A61F 2250/0024
  See application file for complete search history.

(56) References Cited

U.S. PATENT DOCUMENTS

| | | | |
|---|---|---|---|
| 3,788,327 A | 1/1974 | Donowitz et al. |
| 4,886,488 A | 12/1989 | White |
| 5,041,081 A | 8/1991 | Odrich |
| 5,127,901 A | 7/1992 | Odrich |
| 5,171,213 A | 12/1992 | Price, Jr. |

(Continued)

FOREIGN PATENT DOCUMENTS

| | | |
|---|---|---|
| EP | 2 896 386 A1 | 7/2015 |
| WO | 2009/105573 A1 | 8/2009 |

(Continued)

OTHER PUBLICATIONS

International Search Report mailed in PCT/US17/40738 dated Nov. 2, 2017, 4 pages.

(Continued)

*Primary Examiner* — Leslie R Deak
(74) *Attorney, Agent, or Firm* — McDonnell Boehnen Hulbert & Berghoff LLP

(57) ABSTRACT

An apparatus is provided for draining aqueous humor from an eye for reducing intraocular pressure. The draining apparatus comprises a tube defining a passage for fluid flow between an inlet end and an outlet end. An outlet assembly contacts the conjunctival layer externally of the eyeball. The outlet assembly comprises a housing in fluid communication with the outlet end of the tube and having an aperture for allowing egress of aqueous humor onto the external ocular surface. A resistive component is disposed in the housing for providing resistance to a flow of aqueous humor. A pair of tabs project outwardly and are adapted to be disposed subconjunctivally for securing the draining apparatus relative to the eyeball.

7 Claims, 18 Drawing Sheets

(56) References Cited

U.S. PATENT DOCUMENTS

| | | |
|---|---|---|
| 5,300,020 A | 4/1994 | L'Esperance, Jr. |
| 5,346,464 A * | 9/1994 | Camras ............... A61F 9/00781 604/294 |
| 5,626,558 A | 5/1997 | Suson |
| 5,656,026 A | 8/1997 | Joseph |
| 5,743,868 A | 4/1998 | Brown |
| 5,807,302 A | 9/1998 | Wandel |
| 5,830,173 A | 11/1998 | Avery et al. |
| 5,882,327 A | 3/1999 | Jacob |
| 6,077,299 A | 6/2000 | Adelberg et al. |
| 6,261,256 B1 | 7/2001 | Ahmed |
| 6,537,241 B1 | 3/2003 | Odland |
| 6,544,208 B2 | 4/2003 | Ethier et al. |
| 6,558,342 B1 | 5/2003 | Yaron et al. |
| 6,595,945 B2 | 7/2003 | Brown |
| 6,881,198 B2 | 4/2005 | Brown |
| 7,118,547 B2 | 10/2006 | Dahan |
| 7,135,009 B2 | 11/2006 | Tu et al. |
| 7,156,821 B2 | 1/2007 | Dohlman |
| 7,186,233 B2 | 3/2007 | Dohlman |
| 7,192,412 B1 | 3/2007 | Zhou et al. |
| 7,458,953 B2 | 12/2008 | Peyman |
| 7,641,627 B2 | 1/2010 | Camras et al. |
| 7,670,310 B2 | 3/2010 | Yaron et al. |
| 8,579,848 B2 | 11/2013 | Field et al. |
| 8,628,492 B2 | 1/2014 | Lin et al. |
| 8,632,489 B1 | 1/2014 | Ahmed |
| 8,753,305 B2 | 6/2014 | Field et al. |
| 8,986,240 B2 | 3/2015 | Dos Santos et al. |
| 8,998,838 B2 | 4/2015 | Yalamanchili |
| 9,072,588 B2 | 7/2015 | Böhm et al. |
| 9,101,445 B2 | 8/2015 | Bigler et al. |
| 9,132,034 B2 | 9/2015 | Dos Santos |
| 9,155,653 B2 | 10/2015 | Field |
| 9,186,274 B2 | 11/2015 | Camras et al. |
| 9,226,851 B2 | 1/2016 | Gunn |
| 9,259,353 B2 | 2/2016 | Dos Santos et al. |
| 9,333,115 B2 | 5/2016 | Dos Santos |
| 9,339,187 B2 | 5/2016 | Rickard |
| 9,381,301 B2 | 7/2016 | Lattanzio et al. |
| 9,456,924 B2 | 10/2016 | Noroozi et al. |
| 9,492,321 B2 | 11/2016 | Gunn et al. |
| 9,572,712 B2 | 2/2017 | Gunn |
| 9,622,910 B2 | 4/2017 | Field et al. |
| 9,681,983 B2 | 6/2017 | Lind |
| 2002/0143284 A1 | 10/2002 | Tu et al. |
| 2002/0169468 A1 | 11/2002 | Brown |
| 2004/0073156 A1 | 4/2004 | Brown |
| 2004/0127843 A1 | 7/2004 | Tu et al. |
| 2004/0215126 A1 | 10/2004 | Ahmed |
| 2004/0249441 A1 | 12/2004 | Miller et al. |
| 2004/0254521 A1 | 12/2004 | Simon |
| 2005/0049578 A1 | 3/2005 | Tu et al. |
| 2005/0119737 A1 * | 6/2005 | Bene ................... A61F 9/00781 623/4.1 |
| 2005/0240142 A1 | 10/2005 | Dohlman |
| 2005/0240143 A1 | 10/2005 | Dohlman |
| 2006/0036207 A1 | 2/2006 | Koonmen et al. |
| 2006/0069340 A1 | 3/2006 | Simon |
| 2006/0116626 A1 | 6/2006 | Smedley et al. |
| 2006/0189915 A1 | 8/2006 | Camras |
| 2006/0235367 A1 * | 10/2006 | Takashima .......... A61F 9/00781 604/541 |
| 2007/0004998 A1 | 1/2007 | Rodgers et al. |
| 2007/0156079 A1 | 7/2007 | Brown |
| 2007/0254005 A1 | 11/2007 | Pathak et al. |
| 2008/0228127 A1 | 9/2008 | Bums et al. |
| 2009/0036818 A1 | 2/2009 | Grahn et al. |
| 2009/0117166 A1 | 5/2009 | Myung et al. |
| 2009/0326432 A1 | 12/2009 | Schmidt et al. |
| 2010/0056979 A1 | 3/2010 | Smedley et al. |
| 2010/0057055 A1 | 3/2010 | Camras |
| 2010/0114006 A1 | 5/2010 | Baerveldt |
| 2011/0071456 A1 | 3/2011 | Rickard |
| 2011/0105986 A1 | 5/2011 | Bronstein et al. |
| 2012/0302861 A1 | 11/2012 | Marshall et al. |
| 2013/0096483 A1 | 4/2013 | Dacquay |
| 2013/0150775 A1 | 6/2013 | Dos Santos et al. |
| 2013/0150776 A1 | 6/2013 | Bohm et al. |
| 2013/0150777 A1 | 6/2013 | Böhm et al. |
| 2013/0150778 A1 | 6/2013 | Dos Santos |
| 2013/0150779 A1 | 6/2013 | Field |
| 2013/0218064 A1 | 8/2013 | Rickard |
| 2013/0317412 A1 | 11/2013 | Dacquay et al. |
| 2013/0317413 A1 | 11/2013 | Field et al. |
| 2014/0005587 A1 | 1/2014 | Gelvin et al. |
| 2014/0066832 A1 | 3/2014 | Ovchinnikov et al. |
| 2014/0081195 A1 | 3/2014 | Clauson |
| 2014/0163448 A1 | 6/2014 | Lind et al. |
| 2014/0171777 A1 | 6/2014 | Sanchez et al. |
| 2015/0045716 A1 | 2/2015 | Gallardo Inzunza |
| 2015/0057595 A1 | 2/2015 | Gunn et al. |
| 2015/0057596 A1 | 2/2015 | Lind et al. |
| 2015/0057597 A1 | 2/2015 | Johnson et al. |
| 2015/0202082 A1 | 7/2015 | Ilios et al. |
| 2015/0230983 A1 | 8/2015 | Johnson |
| 2015/0230984 A1 | 8/2015 | Gunn |
| 2015/0257931 A1 | 9/2015 | Sanchez et al. |
| 2015/0265469 A1 | 9/2015 | Olson et al. |
| 2016/0033270 A1 | 3/2016 | Camras et al. |
| 2016/0058615 A1 | 3/2016 | Camras et al. |
| 2016/0058616 A1 | 3/2016 | Camras et al. |
| 2016/0067092 A1 | 3/2016 | Lind et al. |
| 2016/0235298 A1 | 8/2016 | Gunn |
| 2016/0242962 A1 | 8/2016 | Torello et al. |
| 2016/0296371 A1 | 10/2016 | Gelvin |
| 2017/0348148 A1 | 12/2017 | Bigler et al. |
| 2017/0348149 A1 | 12/2017 | Stergiopulos et al. |
| 2018/0078416 A1 | 3/2018 | Christiansen |
| 2018/0092774 A1 | 4/2018 | Mehta |

FOREIGN PATENT DOCUMENTS

| | | |
|---|---|---|
| WO | 2013/155252 A1 | 10/2013 |
| WO | 2014/036437 A1 | 3/2014 |
| WO | 2014/130574 A1 | 8/2014 |
| WO | 2016/100500 A1 | 6/2016 |
| WO | 2017/059272 A1 | 4/2017 |
| WO | 2017/106517 A1 | 6/2017 |
| WO | 2018/009556 A1 | 1/2018 |

OTHER PUBLICATIONS

International Search Report mailed in PCT/US16/054828 dated Dec. 13, 2016, 1 page.

International Search Report and Written Opinion mailed in PCT/US18/029717 dated Sep. 21, 2018, 20 pages.

Dohlman et al., "Shunts to Divert Aqueous Humor to Distant Epithelialized Cavities After Keratoprosthesis Surgery", Glaucoma, 2010, 19(2), 111-115.

Molteno et al., "Otago Glaucoma Surgery Outcome Study: Factors Controlling Capsule Fibrosis around Molteno Implants with Histopathological Correlation", The American Academy of Opthalmology, 2003, 110(11), 2198-2206.

\* cited by examiner

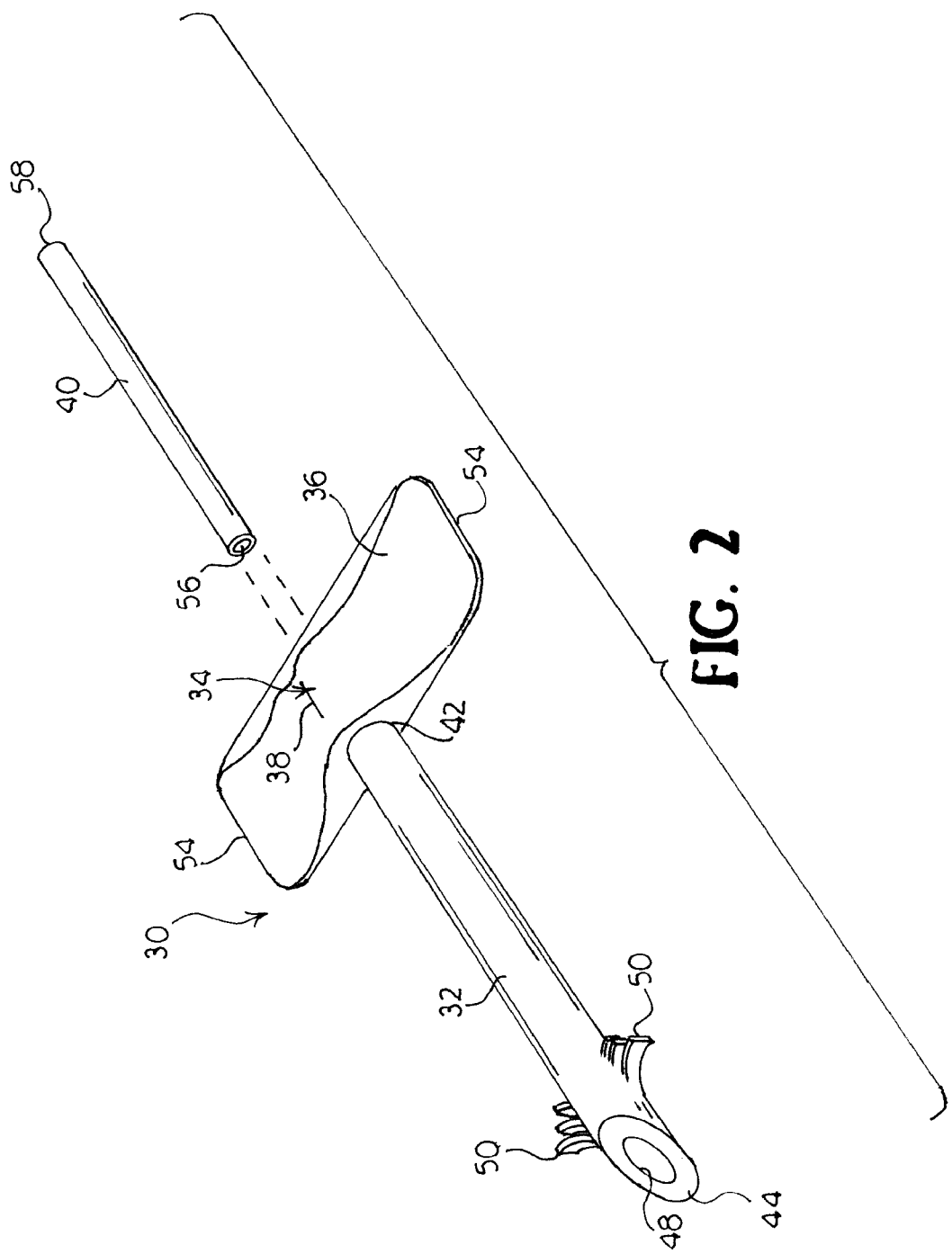

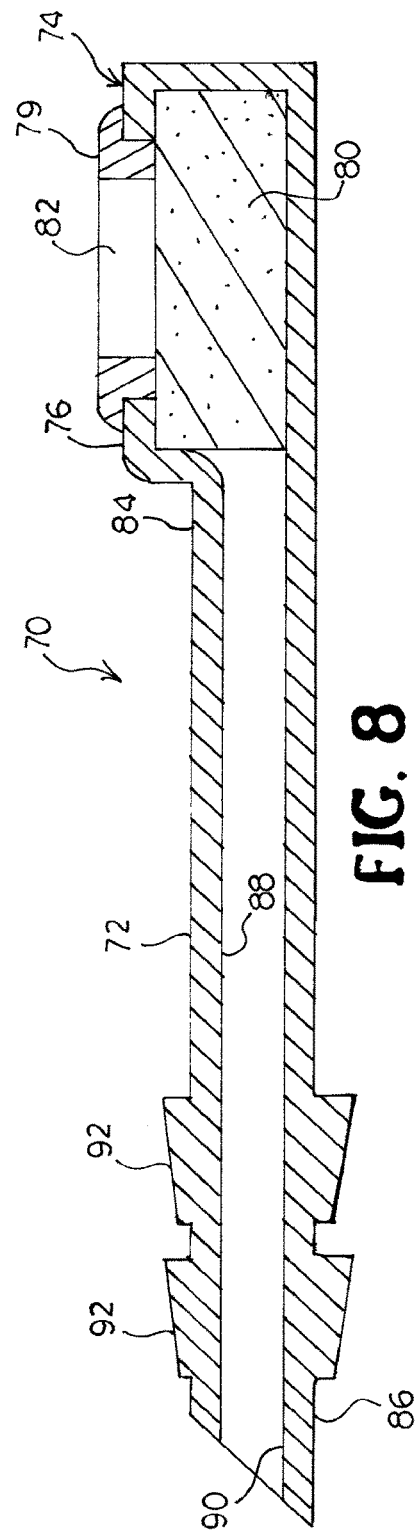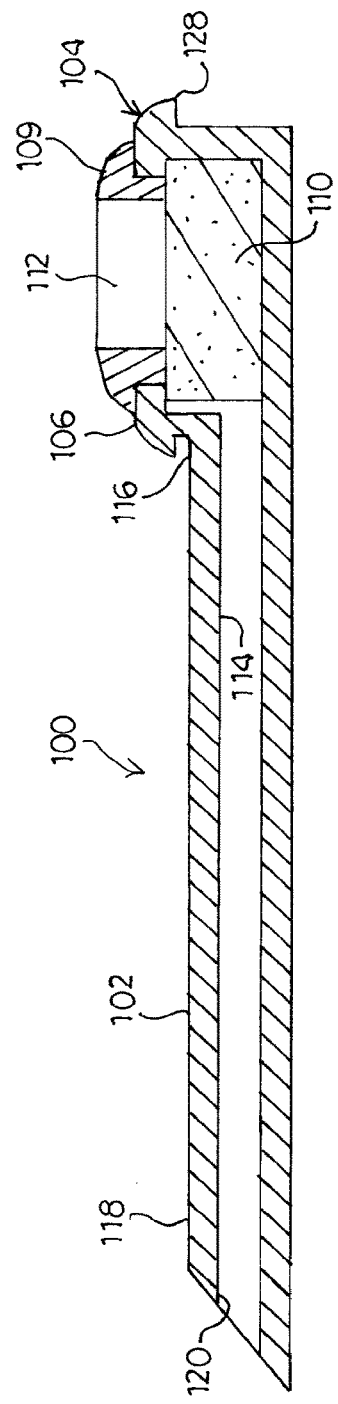

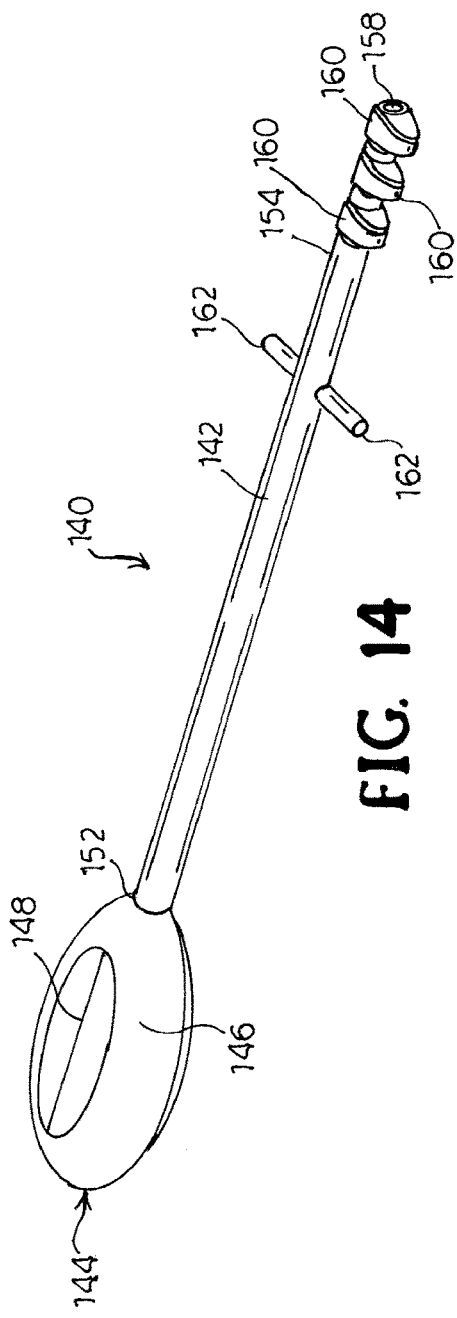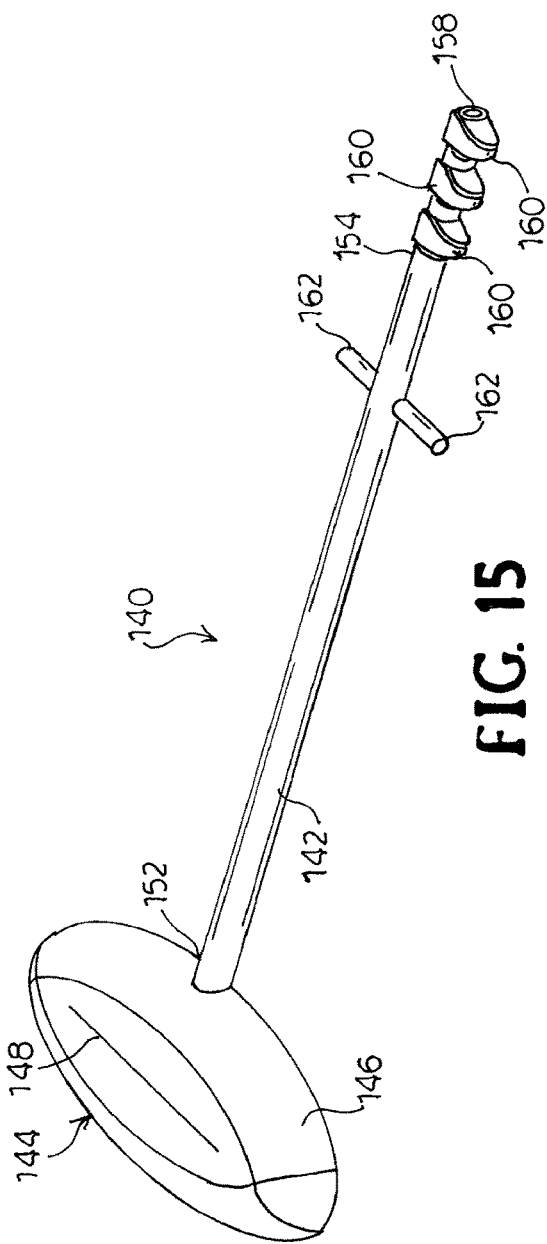

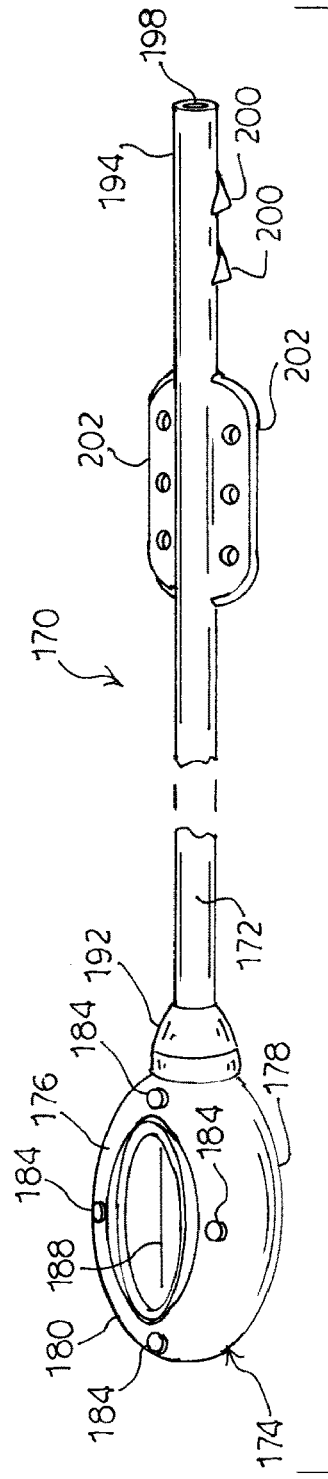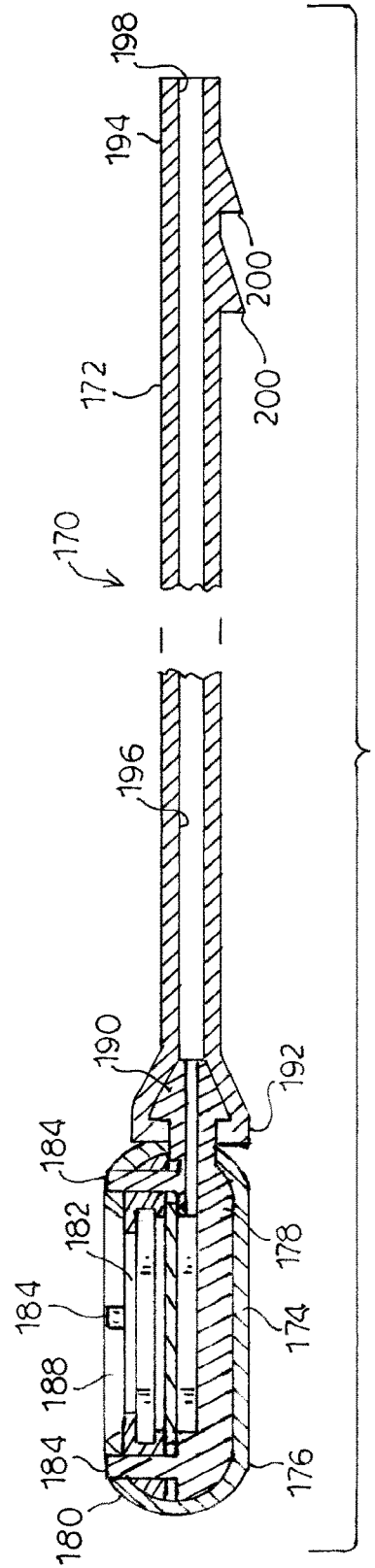

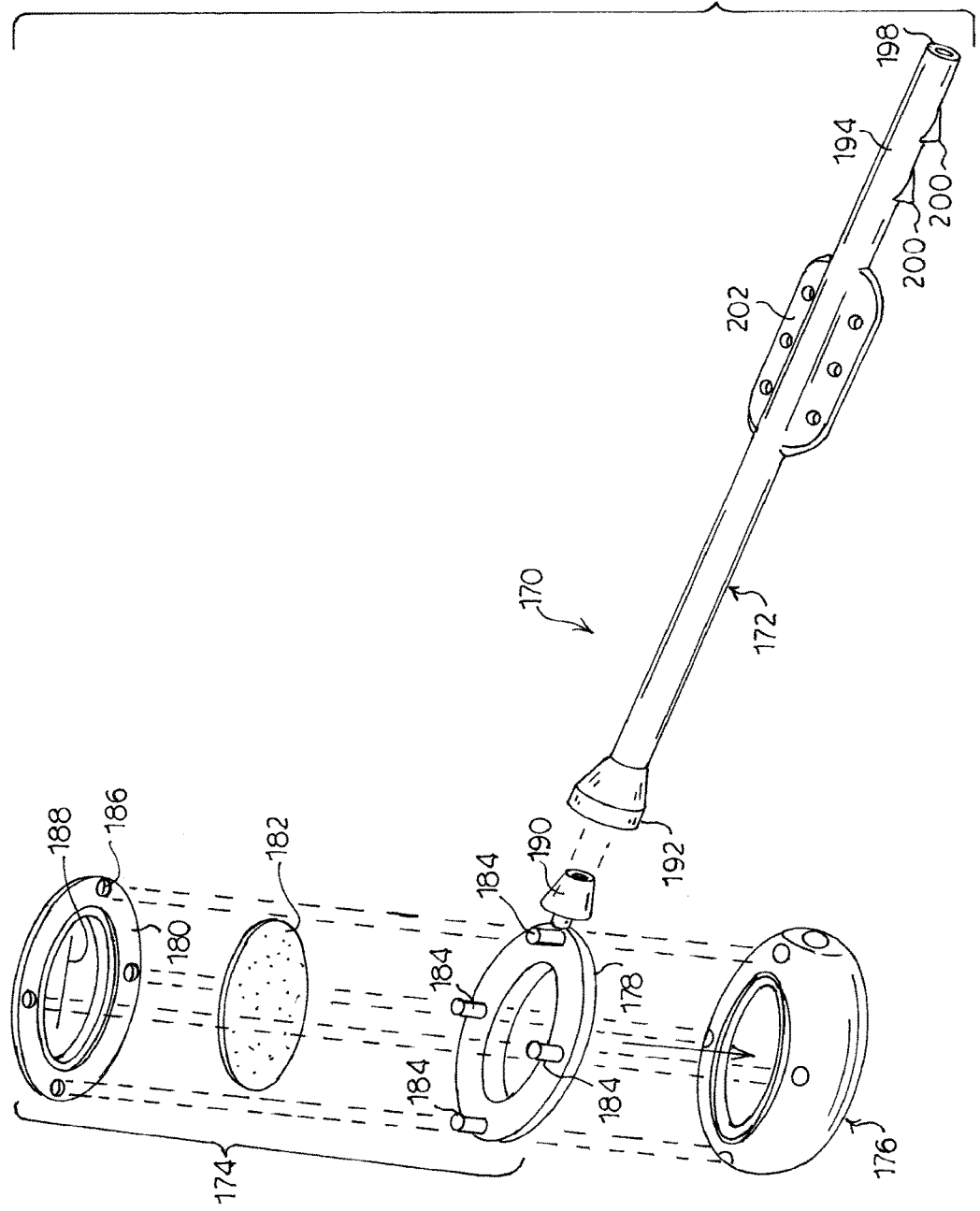

DEVICE AND METHOD FOR REDUCING INTRAOCULAR PRESSURE

CROSS-REFERENCE TO RELATED APPLICATIONS

This application is a continuation of U.S. patent application Ser. No. 14/473,228, filed Aug. 29, 2014, the contents of which are incorporated entirely herein by reference.

BACKGROUND

A device and method are described for draining aqueous humor from the interior of the eye to the exterior of the conjunctiva for reducing intraocular pressure within the eye and, more particularly, an implantable device with a replaceable resistive component is described for regulating the flow of the aqueous humor.

Glaucoma is a group of chronic optic nerve diseases and a leading cause of irreversible blindness. The major risk factor in glaucoma is elevated intraocular pressure due to improper drainage of aqueous humor in the eye. Reduction of intraocular pressure is the only proven treatment to stop the progression of vision loss by reducing stress on the optic nerve.

Standard glaucoma surgeries to reduce intraocular pressure, such as trabeculectomies and glaucoma drainage device implantation, are lengthy and traumatic with unpredictable outcomes and complication rates of 20-60%. Implantable drainage devices function to drain excess aqueous humor from the eye. Installation of a drainage device typically requires a surgical opening made in the sclera to reach the interior of the eye, in particular the anterior chamber or the posterior chamber. The drainage device is then inserted into the interior of the eye for conducting the aqueous humor to the subconjunctival space, herein referred to as subconjunctival shunts, or externally of the conjunctiva, herein referred to as external shunts. A problem associated with subconjunctival shunts is scarring of the bleb in the subconjunctival space affecting its fibrous capsule formation around the outlet, which in many cases requires surgical revision that leads to additional risk of complications. Therefore, there is an ongoing search to identify and utilize alternate drainage sites to avoid many problems associated with bleb and fibrous capsule formations.

External shunts avoid bleb and fibrous capsule formation and the unpredictability of wound healing in the subconjunctival space. However, the outlet of an external shunt may be perceived by the patient as a foreign body, especially those that lie on the corneal surface. These shunts can also be displaced by local tissue motion or extruded by constrictive wound healing processes. One solution secures a subconjunctival portion of the device to the sclera by suturing. However, this technique still leaves the outlet end mobile on the conjunctival surface, which may cause tissue injury and ocular irritation. Moreover, external shunts can expose a mechanical conduit available to transmit microorganisms from the outside to the interior of the eye potentially leading to retrograde infection.

All drainage devices implanted in the eye have the potential to clog from proteins or other substances in the aqueous humor. Clogging reduces permeability of the device and may lead to elevation of intraocular pressure to baseline.

For the foregoing reasons there is a need for a new drainage device for directing aqueous humor from the anterior chamber of an eye to a location external to the eye for reducing and managing intraocular pressure.

SUMMARY

An apparatus is provided for draining aqueous humor from an eye for reducing intraocular pressure. The eye has an anterior chamber and includes a cornea, a surrounding marginal limbus by which the cornea is continuous with a scleral layer and a conjunctival layer, and an exposed ocular surface of the eye and under eyelids. The draining apparatus comprises a tube extending between an inlet end configured to be disposed at the anterior chamber of the eyeball and an outlet end. The tube defines a passage for fluid flow between the inlet end and the outlet end. An outlet assembly having an inner surface and an outer surface is configured to be disposed such that the inner surface contacts the conjunctival layer externally of the eyeball. The outlet assembly comprises a housing defining a cavity in fluid communication with the outlet end of the tube and having an aperture opening into the cavity for allowing egress of aqueous humor onto the external ocular surface. A resistive component is disposed in the cavity of the housing between the outlet end of the tube and the aperture. The resistive component is configured for providing resistance to a flow of aqueous humor for controlling the flow through the tube from the anterior chamber of the eyeball to the external ocular surface. A pair of tabs project outwardly in opposite directions from the housing. The tabs are adapted to be disposed subconjunctivally for securing the draining apparatus relative to the eyeball.

A method for controlling intraocular pressure within the eye is also provided. The method comprises the step of providing a device for draining aqueous humor from the eye. The draining device comprises a tube extending between an inlet end, the tube defining a passage for fluid flow between the inlet end and the outlet end. An outlet assembly has an inner surface and an outer surface and comprises a housing defining a cavity in fluid communication with the outlet end of the tube and having an aperture opening into the cavity for allowing egress of aqueous humor. A resistive component is disposed in the cavity of the housing between the outlet end of the tube and the aperture. The resistive component is configured for providing resistance to a flow of aqueous humor for controlling the flow through the tube from the anterior chamber of the eyeball to the external ocular surface. A pair of tabs project outwardly in opposite directions from the housing. The method for controlling intraocular pressure further comprises the steps of implanting the draining device in the eye such that aqueous humor flows through the tube from the anterior chamber of the eye to the external ocular surface, and securing the tabs under the conjunctival layer.

BRIEF DESCRIPTION OF THE DRAWINGS

For a more complete understanding of the present invention, reference should now be had to the embodiments shown in the accompanying drawings and described below. In the drawings:

FIG. 2 is an exploded perspective view of the drainage device as shown in FIG. 1.

FIG. 8 is a longitudinal cross-section elevation view of the drainage device as shown in FIG. 6.

FIG. 12 is a longitudinal cross-section elevation view of the drainage device as shown in FIG. 10.

FIG. 14 is a perspective view of a fourth embodiment of a drainage device for reducing intraocular pressure.

FIG. 15 is a perspective view of another embodiment of the drainage device as shown in FIG. 14.

FIG. 18 is a perspective view of a fifth embodiment of a drainage device for reducing intraocular pressure.

FIG. 19 is an exploded perspective view of the embodiment of the drainage device as shown in FIG. 18.

FIG. 20 is a longitudinal cross-section of the drainage device as shown in FIG. 18.

DESCRIPTION

Certain terminology is used herein for convenience only and is not to be taken as a limitation on the invention. For example, words such as "upper," "lower," "left," "right," "horizontal," "vertical," "upward," and "downward" merely describe the configuration shown in the FIGs. Indeed, the components may be oriented in any direction and the terminology, therefore, should be understood as encompassing such variations unless specified otherwise.

Figure 1:
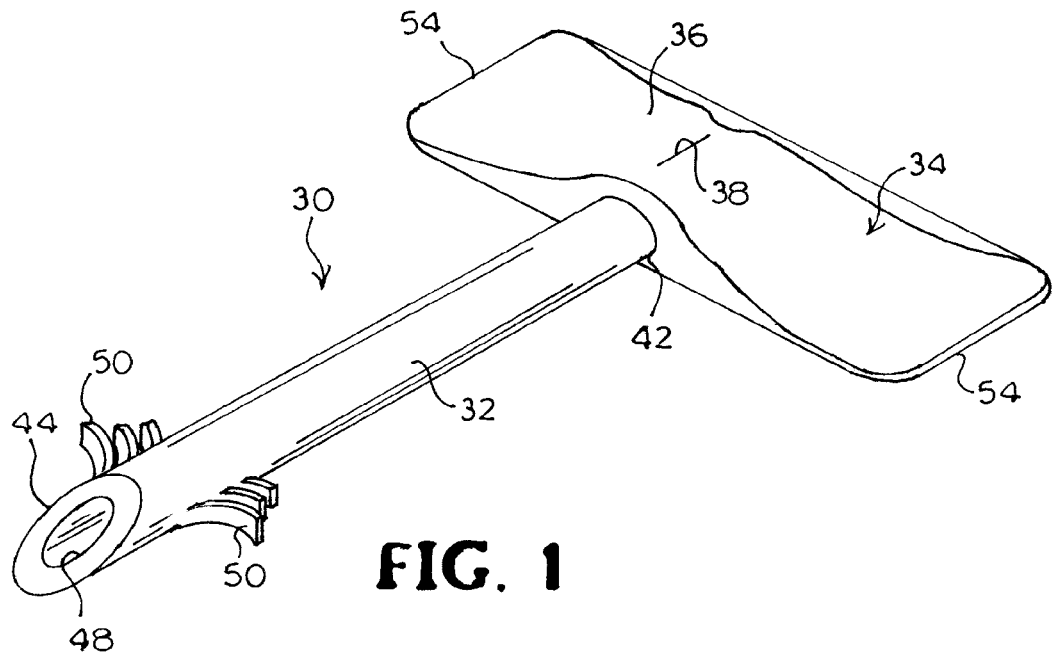
FIG. 1 is a perspective view of an embodiment of a drainage device for reducing intraocular pressure.
Figure 4:
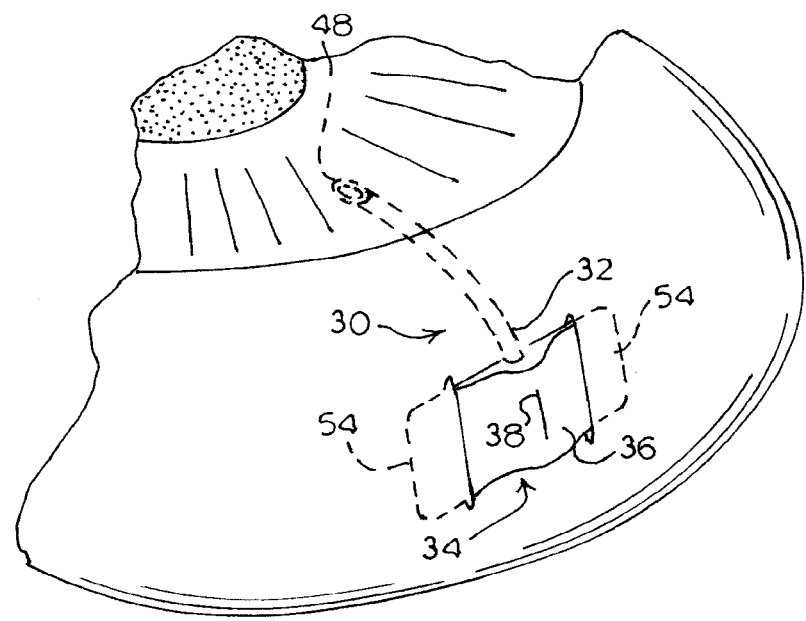
FIG. 4 is a perspective schematic view of the drainage device as shown in FIG. 1 implanted in an eye.
Figure 5:
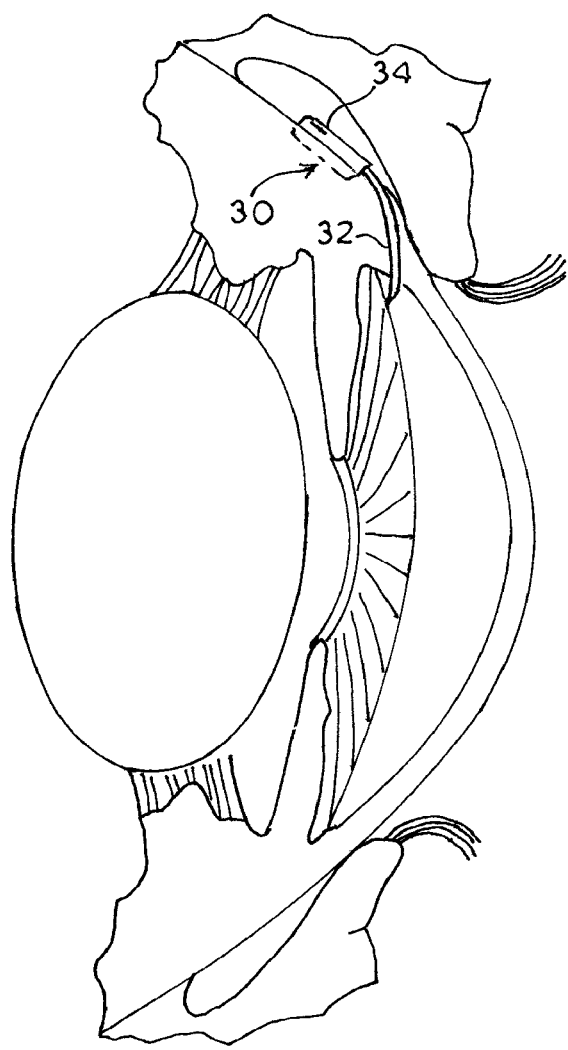
FIG. 5 is a side elevation view of the drainage device implanted in an eye as shown in FIG. 4.
Figure 6:
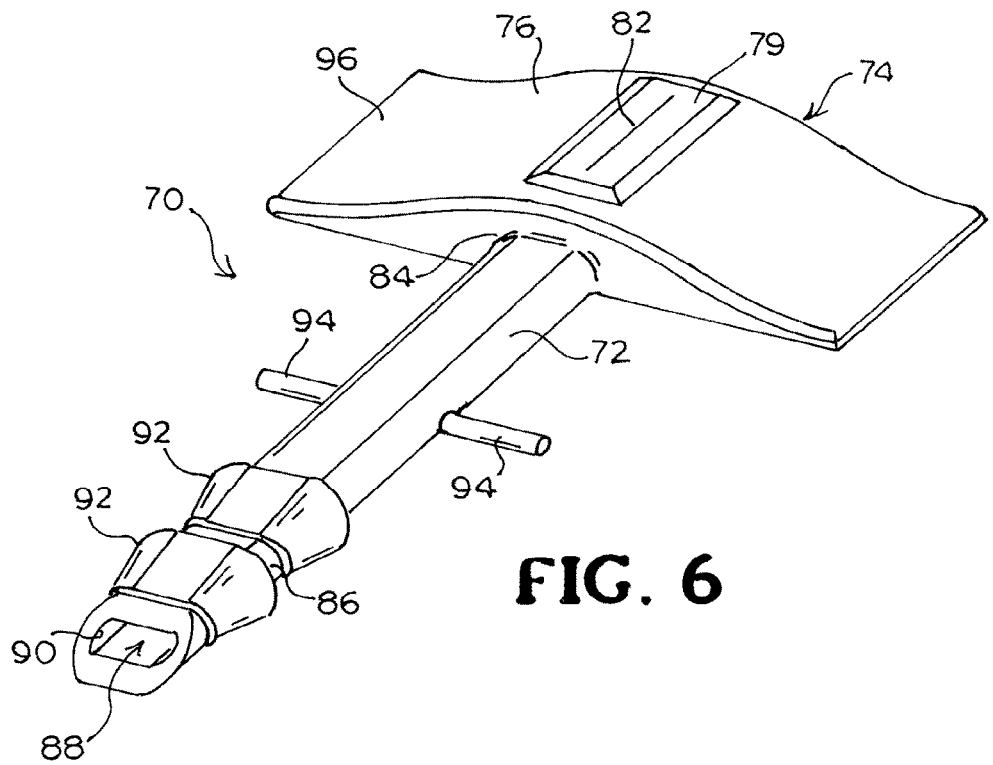
FIG. 6 is a perspective view of another embodiment of a drainage device for reducing intraocular pressure.
Figure 9:
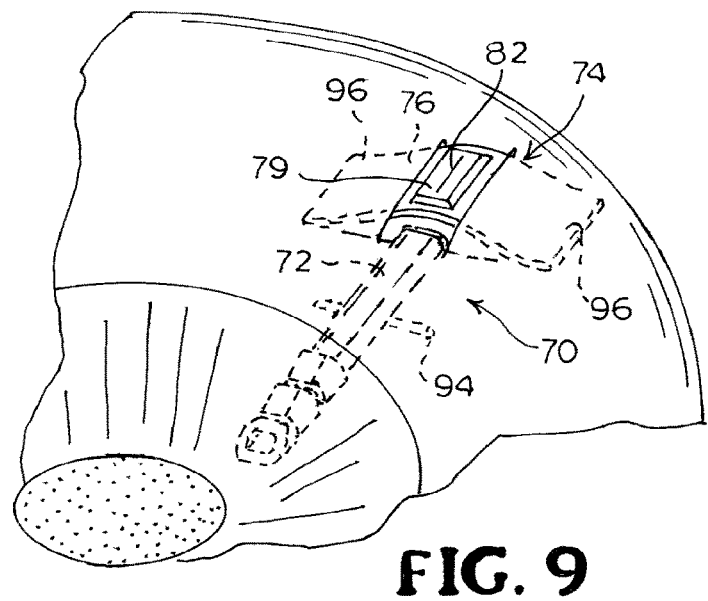
FIG. 9 is a perspective schematic view of the drainage device as shown in FIG. 6 implanted in an eye.
Figure 7:
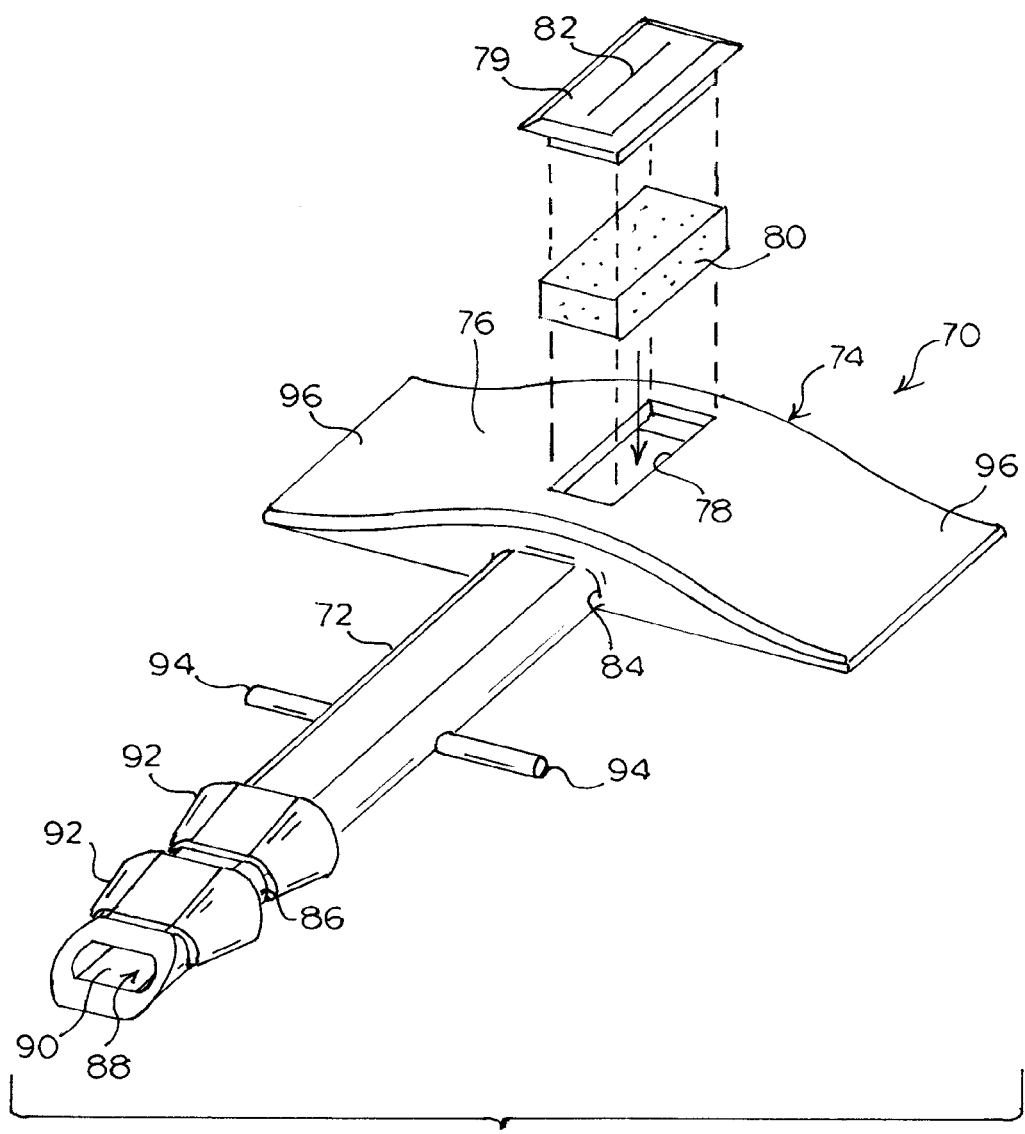
FIG. 7 is an exploded perspective view of the drainage device as shown in FIG. 6.
Figure 10:
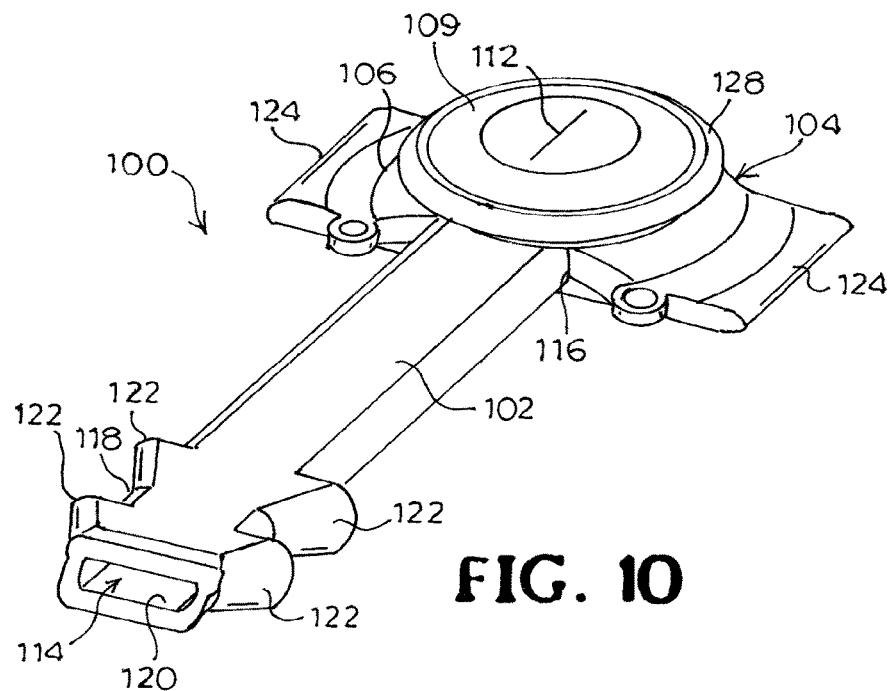
FIG. 10 is a perspective view of a third embodiment of a drainage device for reducing intraocular pressure.
Figure 13:
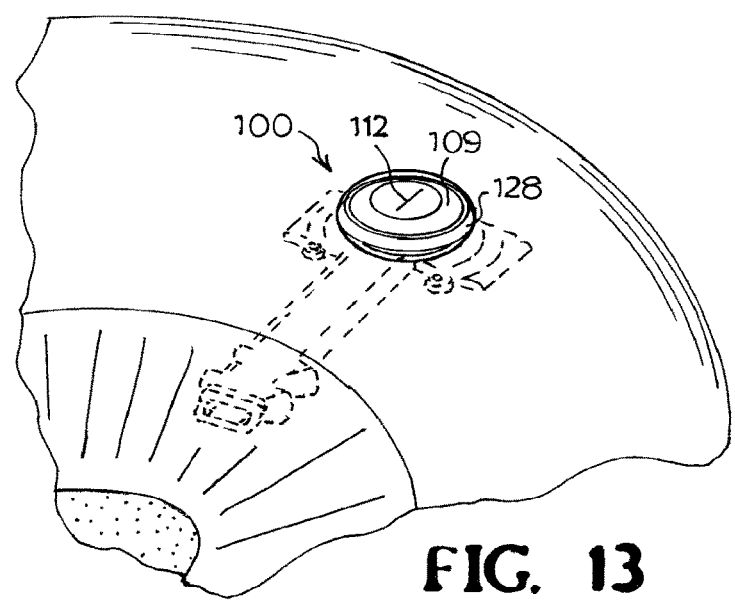
FIG. 13 is a perspective schematic view of the drainage device as shown in FIG. 10 implanted in an eye.
Figure 11:
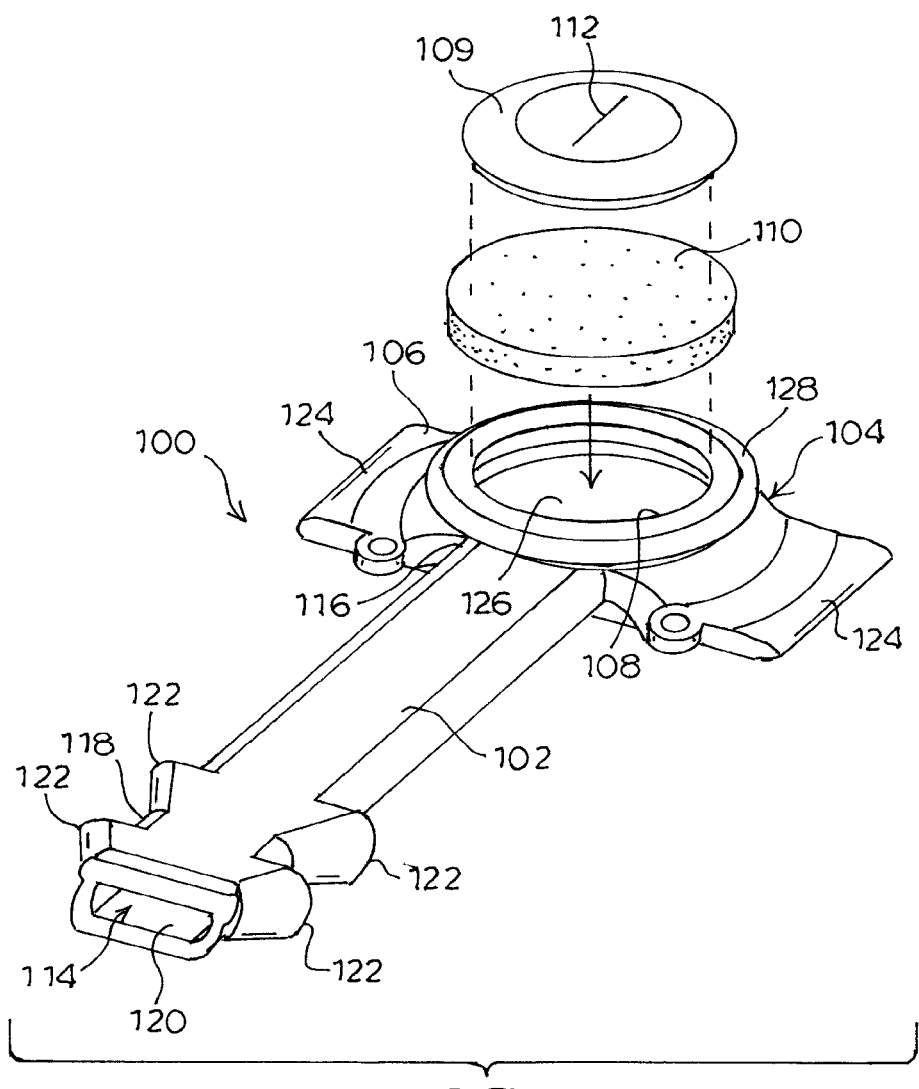
FIG. 11 is an exploded perspective view of the drainage device as shown in FIG. 10.

Referring now to the drawings, wherein like reference numerals designate corresponding or similar elements throughout the several views, an embodiment of an implantable ocular drainage device is shown in FIGS. 1-5 and generally designated at 30. The drainage device 30 comprises a tubular body 32 and an outlet assembly 34, the outlet assembly 34 including a head portion 36 having a valve opening 38 configured for insertion and removal of a filter 40 into the head portion 36. At least a portion of the tubular body 32 of the drainage device 30 is implantable into the anterior chamber of an eye for draining aqueous humor (FIGS. 4 and 5). As will be described below, the filter 40 and the valve 38 are configured, separately or in combination, to function to maintain and control intraocular pressure and allow the aqueous humor dynamics to behave more physiologically.

The tubular body 32 of the drainage device 30 is substantially cylindrical and has a proximal end 42 and a distal end 44. The body 32 defines a lumen 46 that extends between the proximal end 42 and the distal end 44 with the distal end having at least one opening 48 communicating with the lumen 46. The opening 48 functions as a fluid inlet at the distal end 44 of the body 32. The distal end 44 of the body 32 is beveled for easy entry into the anterior chamber of the eye.

The lumen 46 forms at least a portion of a flow path that permits the drainage of aqueous humor from the anterior chamber of the eye to the external surface of the eye. The body 32 has a length sufficient to provide fluid communication between the anterior chamber of the eye and the fornix or cul-de-sac region under the eyelid to allow aqueous humor to flow from the anterior chamber through the lumen 46 and into the tear film when the drainage device 30 is implanted in the eye. For this purpose, the body 32 of the drainage device 30 must have a minimum length of at least about 3 mm for the outlet assembly 34 to reach the fornix or cul-de-sac region under the eyelid. In one embodiment, the body 32 may have a length of between about 4 mm and about 9 mm for adult humans. In use, the body 32 lies substantially underneath the conjunctiva with distal end in the anterior or posterior chamber of the eye as best see in FIGS. 4 and 5.

The transverse cross-sectional shape of the body 32, in addition to circular as shown in FIGS. 1-5, may be other suitable shapes such as, for example, oval, square, trapezoidal, rectangular, or any combination thereof. Regardless of shape, the cross-sectional size of the lumen 46 within the body 32 may vary to selectively alter fluid flow characteristics. For example, a small cross-sectional size can be used to restrict fluid flow. In one embodiment, the cross-sectional size of the lumen 46 may range, for example, from about 0.05 mm to about 1.0 mm.

One or more barbs 50 may be provided adjacent the distal end 44 of the body 32. The barbs 50 can extend from a portion of the outer surface of the body 32 for contact with the sclera when the drainage device 30 is implanted. The barbs 50 are adapted to engage with the sclera and provide stability until biointegration of the body 32 within the subconjunctival space. The barbs 50 may be formed as part of the body 32 of the drainage device 30 during manufacture or may be subsequently fused or bonded to the body 32 by suitable means known in the art.

Figure 3:
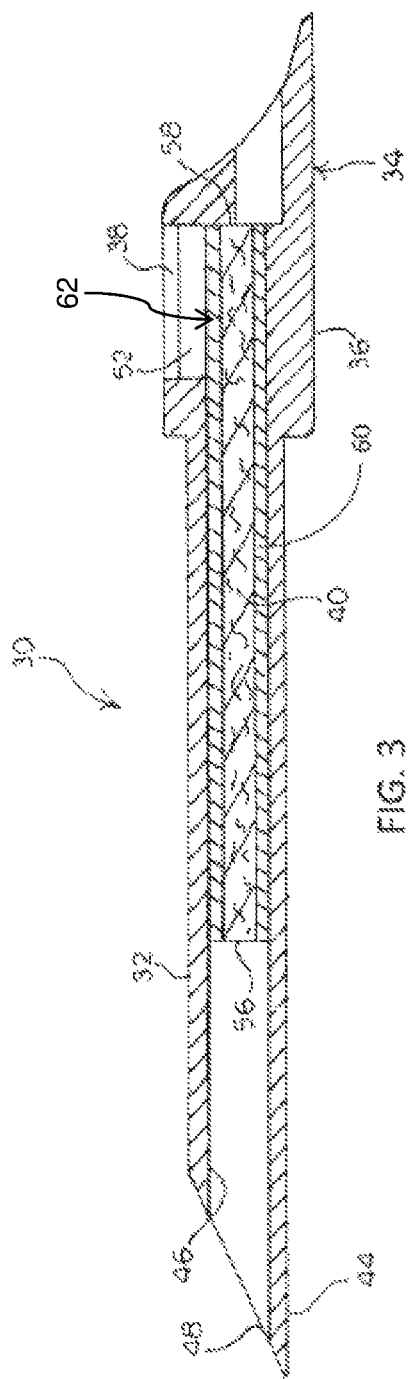
FIG. 3 is a longitudinal cross-section elevation view of the drainage device as shown in FIG. 1.

Referring to FIG. 3, the head portion 36 of the outlet assembly 34 defines an interior cavity 52. The head portion 36 is integral with, or attached to, the proximal end 42 of the body 32 such that the cavity 52 is in fluid communication with the lumen 46 of the body 32. In the embodiment shown, the head portion 36 and the body 32 may be formed integrally as a unit. Alternatively, each component may be separate from the others. The head portion 36 may be dome-shaped to provide a continuous transition surface from along an outer surface of the head portion 36 to the surface of the eye. This shape may also be well tolerated by the eyelid of the patient. It is understood, however, that other shapes of the head portion 36 may be suitable for providing the same advantages. For example, a minimally protruding, substantially flat head portion 36 with rounded edges may be equally well tolerated. Other appropriate designs may be determined by those skilled in the art. The inner surface of the head portion 36 may be flat or curved, as appropriate, to correspond to the shape of the external surface of the sclera where the drainage device 30 is to be positioned.

The head portion 36 may further comprise integral radial tabs 54 extending outwardly from a longitudinal axis of the drainage device 30. Alternatively, the tabs 54 may be separate pieces attached to the head portion 36. If the tabs 54 are separate pieces, they may be comprised of a flexible biocompatible material, such as silicone or polyurethane, that can easily deform to follow eye movement. As will be described below, the tabs 54 function to stabilize the position of the drainage device 30 and prevent extrusion or pultrusion of the drainage device 30 from its intended location and reduce ocular surface irritation and conjunctival erosion.

Referring to FIGS. 2 and 3, the filter 40 is an elongate member having a distal inflow end 56 and a proximal outflow end 58. As shown in FIG. 3, the filter 40 is at least partially disposed within the head portion 36 and the lumen 46 at the proximal end 42 of the body 32 of the drainage device 30. The filter 40 is configured such that the lumenal passage of the body 32 is closed or substantially closed by the filter 40. The filter 40 functions to prevent bacterial migration and may be used to regulate intraocular pressure by providing a predetermined resistance to outflow of aqueous humor from the anterior chamber of the eye into the tear film. As a resistive component, the filter can provide particular flow rate of aqueous humor by selecting a filter having predetermined number and size of pores and a selected overall length of the filter 40 (i.e., the flow path). These parameters provide an appropriate resistance to flow sufficient to reduce and maintain intraocular pressure while preventing ocular hypotony. The filter 40 may have a gradient of pore sizes along the length of the filter 40. For example, the pore size may continually decrease from the distal end 56 of the filter 40 to the proximal end 58 in order to prevent debris accumulation at the distal end 56 of the filter 40. Larger pores sizes at the distal end 56 and the proximal end 58 of the filter 40 provide a pore gradient to reduce the effect of clogging on the outflow resistance.

The filter 40 may be removable and replaceable because access to the outlet assembly 34 is available without disrupting the position of the drainage device 30 in the eye. The filter 40 can be replaced to, for example, adjust the ocular pressure by selecting a filter configuration that provides a selected aqueous humor flow rate. Alternatively, the filter 40 may be configured to form a permanent element of the drainage device 30.

The filter 40 may optionally be provided with a rigid outer sheath 60. In one embodiment, the outer sheath 60 is rigid enough to provide support to the filter 40 in order to assist installation and removal of the filter 40 relative to the head portion 36 and to improve the durability of the filter 40. In one embodiment, the sheath 60 is a hollow mesh cage having a plurality of openings 62 along its perimeter. The openings 62 provide passageways for egress of aqueous humor draining through the filter 40. However, the outer sheath 60 is not limited to this configuration as long as the aqueous humor can pass. For example, the outer sheath 60 may only have one or more openings through a sidewall, or one or more openings through the sidewall and an end wall. The outer sheath 60 may be formed from nitinol, polyimide, or other similar material, such that the combined filter 40 and sheath 60 are expandable following installation to improve sealing of the lumen 46 or the outlet assembly 34.

In one embodiment, the valve 38 comprises a linear slit partially axially traversing the head portion 36 and opening into the interior cavity 52. The slit valve 38 permits the outflow of aqueous humor that has passed through the lumen 46 and the filter 40 to flow onto the sclera and enter the tear film. The slit valve 38 also resists bacterial incursion. While the slit valve 38 depicted in the FIGs. is a single elongate linear aperture, it is understood that other slit configurations may be suitable for providing resistance to aqueous humor outflow and restriction against bacterial incursion. For example, an irregular slit or a plurality of smaller slits may be used, or the slit or plurality of slits may be less elongated and more rounded than shown. A polymer microfluidic passageway in the form of a slit, or a plurality of slits or holes, is also suitable.

The slit valve 38 opens and closes to regulate flow from the interior cavity 52 of the head portion 36 to the external surface of the eye while maintaining the intraocular pressure within the normal range of about 7 mmHg to about 20 mmHg. For example, when the intraocular pressure exceeds a first predetermined pressure, the slit valve 38 will open and permit fluid to exit the outlet assembly 34. When the intraocular pressure reaches a second, lower pressure, the slit valve 38 will close and limit, or inhibit, fluid from exiting the head portion 34. The slit valve 38 will remain closed until the intraocular pressure again reaches the first pressure, and at which time the slit valve 38 will reopen to permit, or enhance, drainage of fluid.

Accordingly, the drainage device 30 provides drainage of the anterior chamber of the eye through the drainage device based on the intraocular pressure and reduces the likelihood for over-draining the anterior chamber and causing hypotony. Additionally, the slit valve 38, with its check valve structure, prevents backflow of the aqueous humor. It is understood that any type of conventional pressure-controlled check valve may be used as long as it has a structure suitable this application.

Referring now to FIGS. 6-9, another embodiment of an implantable ocular drainage device is shown and generally designated at 70. The drainage device 70 comprises a tubular body 72 and an outlet assembly 74, the outlet assembly 74 including a head portion 76 having a rectangular opening 78 configured for insertion and removal of a filter 80 into the head portion 76. A removable rectangular cap 79 having a valve 82 is provided for sealing the opening 78 and for accessing the interior of the head portion 76. At least a portion of the tubular body 72 of the drainage device 70 is implantable into the anterior chamber of an eye for draining aqueous humor.

The tubular body 72 of the drainage device 70 is substantially ovular and has a proximal end 84 and a distal end 86. The body 72 defines a lumen 88 that extends between the proximal end 84 and the distal end 86 with the distal end having at least one opening 90 communicating with the lumen 88 and functioning as a fluid inlet. One or more tapered projections 92, or barbs, may be provided adjacent the distal end 86 of the body 72. A pair of opposed suture bars 94 extend outwardly from the body 72 intermediate along the body 72 between the head portion 76 and the barbs 92.

The head portion 76 of the outlet assembly 74 may further comprise integral radial tabs 96 extending outwardly from a longitudinal axis of the drainage device 30. Referring to FIG. 8, the head portion 76 defines an interior cavity 96 in fluid communication with the lumen 88 of the body 72. The interior cavity 96 is configured for accommodating the filter 80. The filter 40 is disposed within the head portion 76 and is configured such that the outlet of the lumenal passage of the body 72 is closed or substantially closed by the filter 80. The filter 80 functions to prevent bacterial migration and may be used to regulate intraocular pressure by providing a predetermined resistance to outflow of aqueous humor from the anterior chamber of the eye into the tear film. The valve 82 in the cap 79 permits the outflow of aqueous humor that has passed through the filter 80 to flow onto the sclera and enter the tear film while providing resistance to aqueous humor outflow and restriction against bacterial incursion.

A third embodiment of an implantable ocular drainage device is shown in FIGS. 10-13, and generally designated at 100. The drainage device 100 comprises a tubular body 102 and an outlet assembly 104, the outlet assembly 104 including a head portion 106 defining a circular opening 108 configured for insertion and removal of a filter 110 into the head portion 106. A removable circular cap 109 having a valve 112 is provided for sealing the opening 108 and for accessing the interior of the head portion 106. At least a portion of the tubular body 102 of the drainage device 100 is implantable into the anterior chamber of an eye for draining aqueous humor.

The tubular body 102 of the drainage device 100 is substantially ovular and defines a lumen 114 that extends between a proximal end 116 and the distal end 118 of the body. The distal end 118 of the body 102 has at least one opening 120 communicating with the lumen 114 and functioning as a fluid inlet. One or more tapered projections 122, or barbs, may be provided adjacent the distal end 118 of the body 102.

The head portion 106 of the outlet assembly 104 may further comprise integral radial tabs 124 extending outwardly from a longitudinal axis of the drainage device 100. Referring to FIG. 12, the head portion 106 defines an interior cavity 126 in fluid communication with the lumen 114 of the body 102. The interior cavity 126 is configured for accommodating the filter 110. A circular rim 128 extends outwardly of the surface of the head portion 106 for defining the opening 120. The filter 110 is disposed within the head portion 106 and is configured such that the outlet of the lumenal passage of the body 102 is closed or substantially closed by the filter 110. The filter 110 functions to prevent bacterial migration and may be used to regulate intraocular pressure by providing a predetermined resistance to outflow of aqueous humor from the anterior chamber of the eye into the tear film. The valve 112 in the cap 109 permits the outflow of aqueous humor that has passed through the filter 110 to flow onto the sclera and enter the tear film while providing resistance to aqueous humor outflow and restriction against bacterial incursion.

Referring now to FIGS. 14-17, a fourth embodiment of an implantable ocular drainage device is shown and generally designated at 140. The drainage device 140 comprises a tubular body 142 and an outlet assembly 144, the outlet assembly 144 including an ovular head portion 146 having an opening 148 for accommodating a filter 150. In one embodiment of the drainage device 140, the longitudinal axis of the head portion 146 is coaxial with the longitudinal axis of the body 142 (FIG. 14). In another embodiment, the longitudinal axis of the head portion 146 is substantially perpendicular to the longitudinal axis of the body 142 (FIG. 15). At least a portion of the tubular body 142 of the drainage device 140 is implantable into the anterior chamber of an eye for draining aqueous humor.

The tubular body 142 of the drainage device 140 is substantially circular and has a proximal end 152 and a distal end 154. The body 142 defines a lumen 156 that extends between the proximal end 152 and the distal end 154, with the distal end having at least one opening 156 communicating with the lumen 156 and functioning as a fluid inlet. One or more radial projections 160, or barbs, may be provided adjacent the distal end 154 of the body 142. A pair of opposed suture bars 162 extend outwardly from the body 142 intermediate along the body 142 between the head portion 146 and the barbs 160.

Figure 16:
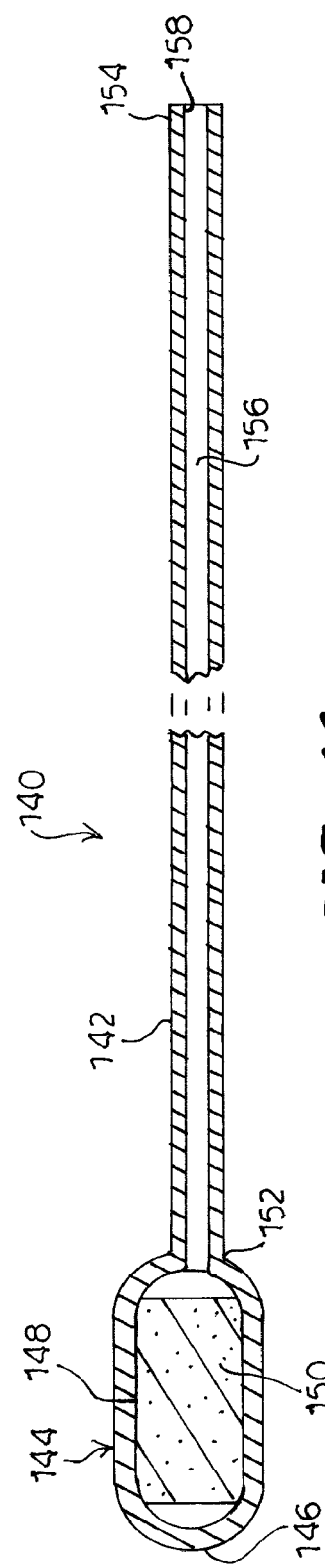
FIG. 16 is a longitudinal cross-section elevation view of the drainage device as shown in FIG. 14.
Figure 17:
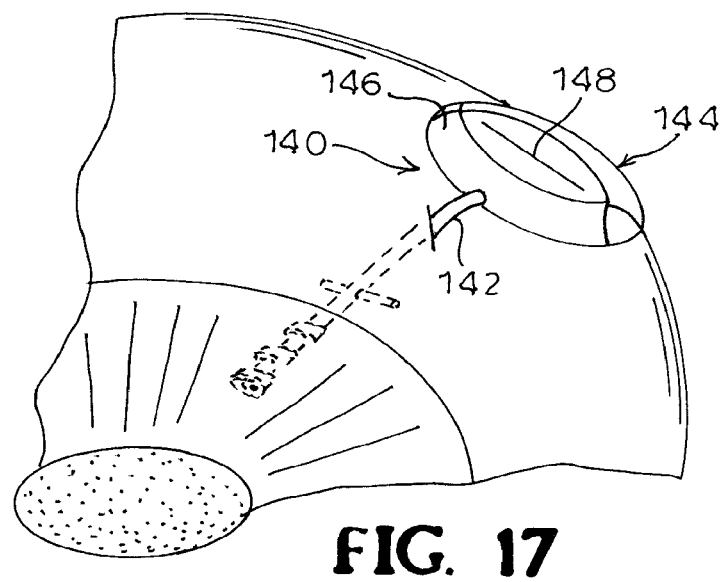
FIG. 17 is a perspective schematic view of the drainage device as shown in FIG. 15 implanted in an eye.
Figure 21:
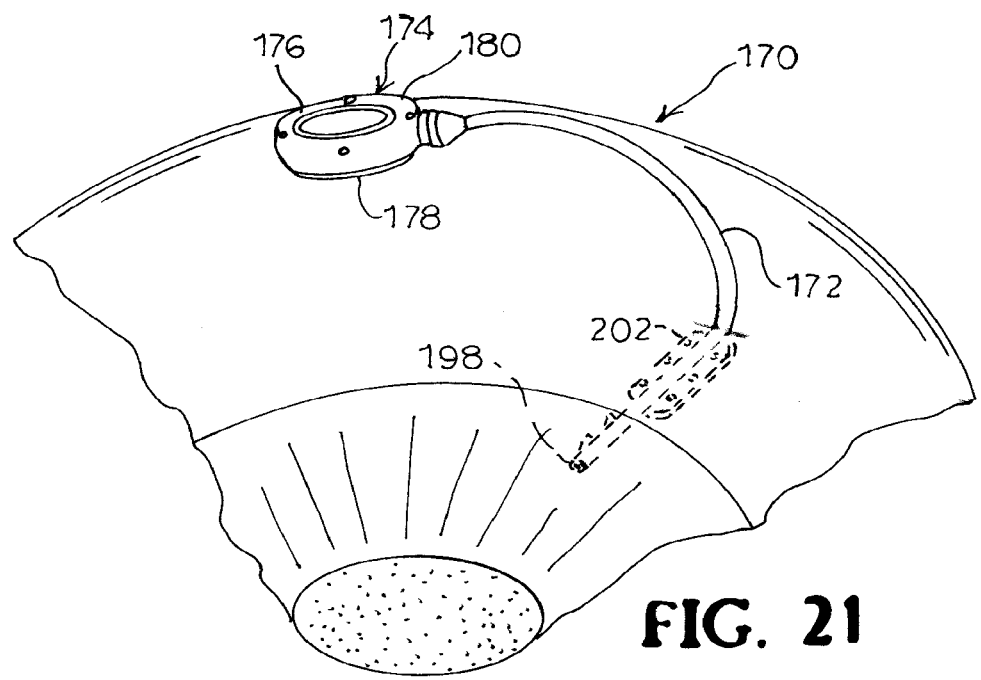
FIG. 21 is a perspective schematic view of the drainage device as shown in FIG. 18 implanted in an eye.

The head portion 146 defines an interior cavity 164 in fluid communication with the lumen 156 of the body 142 for accommodating the filter 150. Referring to FIG. 16, the filter 150 is disposed within the head portion 146. The filter 150 is configured such that the lumenal passage of the body 142 is closed or substantially closed by the filter 150. The filter 150 functions to prevent bacterial migration and may be used to regulate intraocular pressure by providing a predetermined resistance to outflow of aqueous humor from the anterior chamber of the eye into the tear film. The opening 148 in the form of slit valve 148 permits the outflow of aqueous humor that has passed through the filter 150 to flow onto the tear film. The slit valve 148 also resists bacterial incursion and may be suitable for providing resistance to aqueous humor outflow.

Referring now to FIGS. 18-21, a fifth embodiment of an implantable ocular drainage device is shown and generally designated at 170. The drainage device 170 comprises a tubular body 172 and an outlet assembly 174, the outlet assembly 174 including an ovular head portion 176. The head portion 176 comprises a base 178, a cap 180 and a filter 182. The base 178 includes four perimeter posts 184 configured to be received in corresponding holes 186 in the cap 180. The assembled base 178 and cap 180 define an interior cavity for accommodating the filter 182. The cap 180 has a slit valve 188 opening into the cavity in the head portion 176.

The tubular body 172 of the drainage device 170 is substantially circular in transverse cross-section and has a proximal end 192 and a distal end 194. The body 172 defines a lumen 196 that extends between the proximal end 192 and the distal end 194. A plug 190 operatively connects the proximal end 192 of the body 172 for fluid communication with the outlet assembly 174. The filter 182 is disposed within the head portion 146 such that the lumenal passage of the body 172 is closed or substantially closed by the filter 182. The filter 182 functions to prevent bacterial migration and may be used to regulate intraocular pressure by providing a predetermined resistance to outflow of aqueous humor from the anterior chamber of the eye into the tear film. At least one opening 198 at the distal end 194 of the body 172 communicates with the lumen 196 and functions as a fluid inlet. At least a portion of the tubular body 142 of the drainage device 140 is implantable into the anterior chamber of an eye for draining aqueous humor.

One or more radial barbs 200 may be provided adjacent the distal end 194 of the body 172. A pair of opposed longitudinal suture wings 202 extend radially outwardly from the body 172 intermediate along the length of the body 172 between the head portion 176 and the barbs 200.

Figure 22:
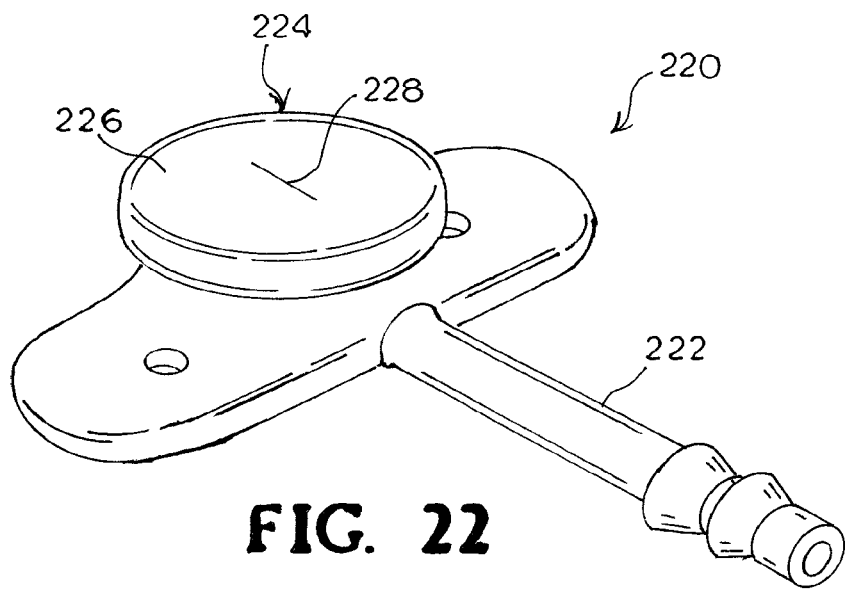
FIG. 22 is a perspective view of a sixth embodiment of a drainage device for reducing intraocular pressure.
Figure 23:
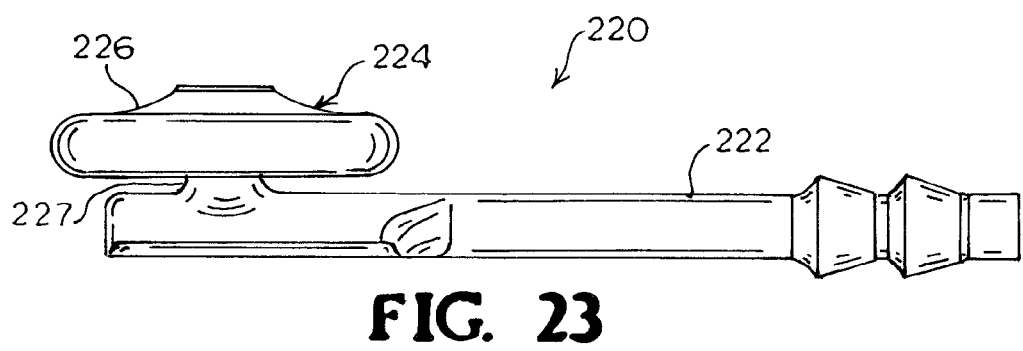
FIG. 23 is a side elevation view of the embodiment of the drainage device as shown in FIG. 22.

A sixth embodiment of an implantable ocular drainage device is shown in FIGS. 22 and 23, and generally designated at 220. The drainage device 220 comprises a tubular body 222 and an outlet assembly 224. The outlet assembly 224 includes a generally circular head portion 226 defining a slit valve 228. As described in previous embodiments, the head portion 226 defines a cavity for accommodating a filter (not shown). The head portion 226 may further comprise integral radial tabs 230 extending outwardly from a longitudinal axis of the drainage device 220. At least a portion of the tubular body 222 of the drainage device 220 is implantable into the anterior chamber of an eye for draining aqueous humor to the external surface of the eye. Referring to FIG. 23, the head portion 226 of the outlet assembly 224 defines a short conduit 227 between the head portion 226 and the body 222. The conduit 227 is in fluid communication with the lumen of the body 222 for accommodating fluid flow from the body 222 and into the head portion 226.

Figure 24:
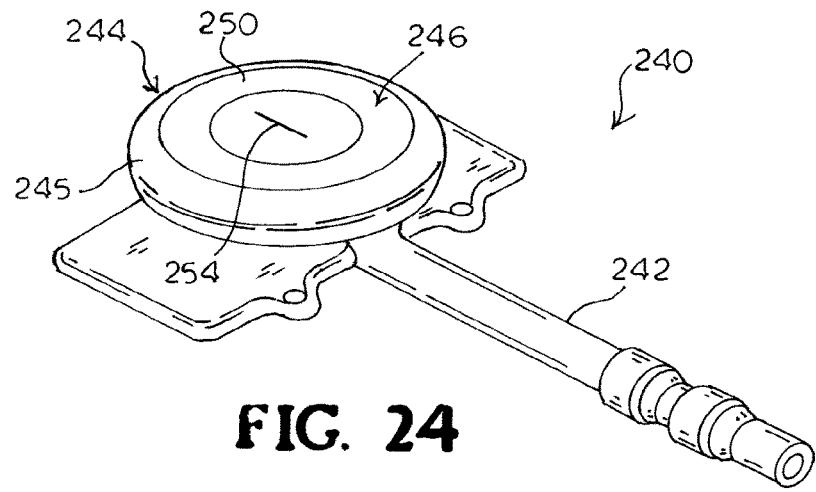
FIG. 24 is a perspective view of a seventh embodiment of a drainage device for reducing intraocular pressure.
Figure 25:
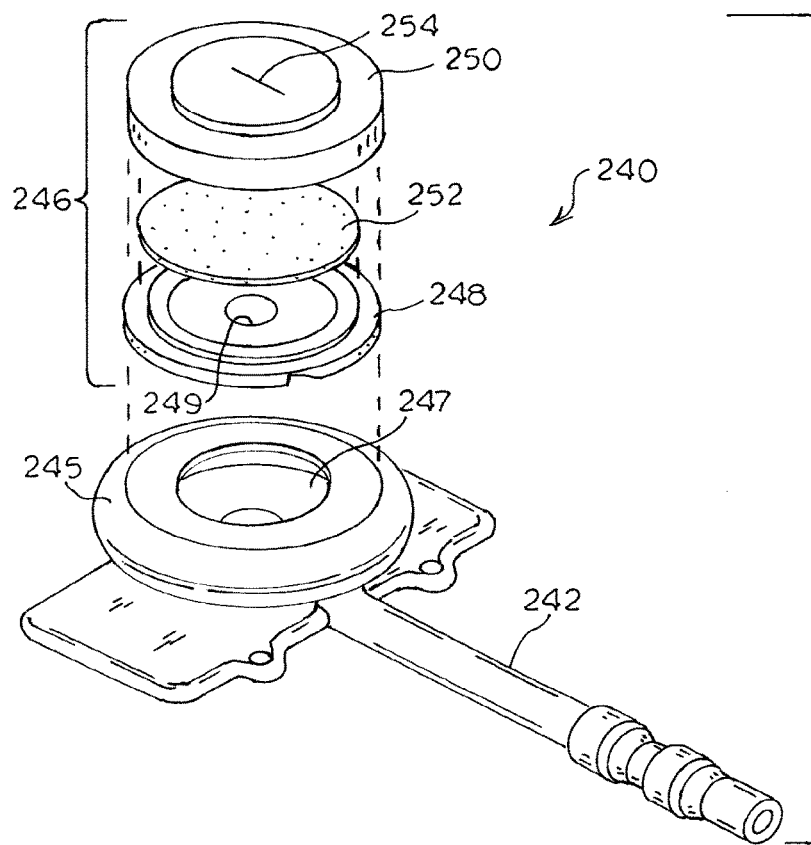
FIG. 25 is an exploded perspective view of the embodiment of the drainage device as shown in FIG. 24.
Figure 26:
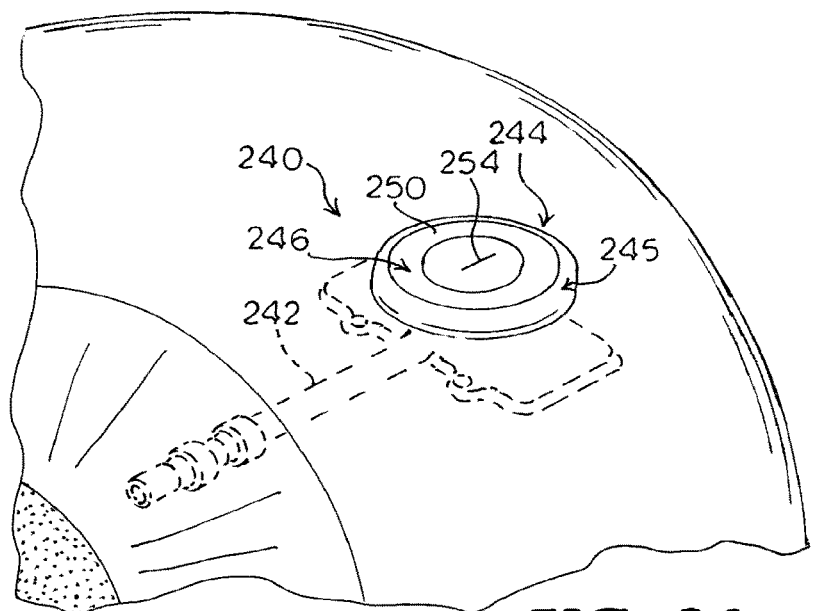
FIG. 26 is a perspective schematic view of the drainage device as shown in FIG. 24 implanted in an eye.

A seventh embodiment of an implantable ocular drainage device is shown in FIGS. 24-26, and generally designated at 240. The drainage device 240 comprises a tubular body 242 and an outlet assembly 244. The outlet assembly 244 includes a generally circular head portion 245 defining a recess 247 for accommodating a removable circular disc 246. The disc 246 comprises a base 248, a cap 250 and a filter 252. The assembled base 248 and cap 250 define an interior cavity for accommodating the filter 252 therebetween. The base 248 includes in inner circular flange 249 for supporting the filter 252 spaced from a central inlet opening 249 in the base 248. The cap 250 has a slit valve 254 opening into the cavity in the disc 246 for allowing aqueous humor to pass from the disc.

The filter 252 is disposed within the head portion 245 and is sealed against the flange 249 such that the inlet 249 into the cavity is closed or substantially closed by the filter 252. The filter 252 functions to prevent bacterial migration and may be used to regulate intraocular pressure by providing a predetermined resistance to outflow of aqueous humor from the anterior chamber of the eye into the tear film. The valve 254 in the cap 250 permits the outflow of aqueous humor that has passed through the filter 252 to flow onto the sclera and enter the tear film while providing resistance to aqueous humor outflow and restriction against bacterial incursion.

Figure 29:
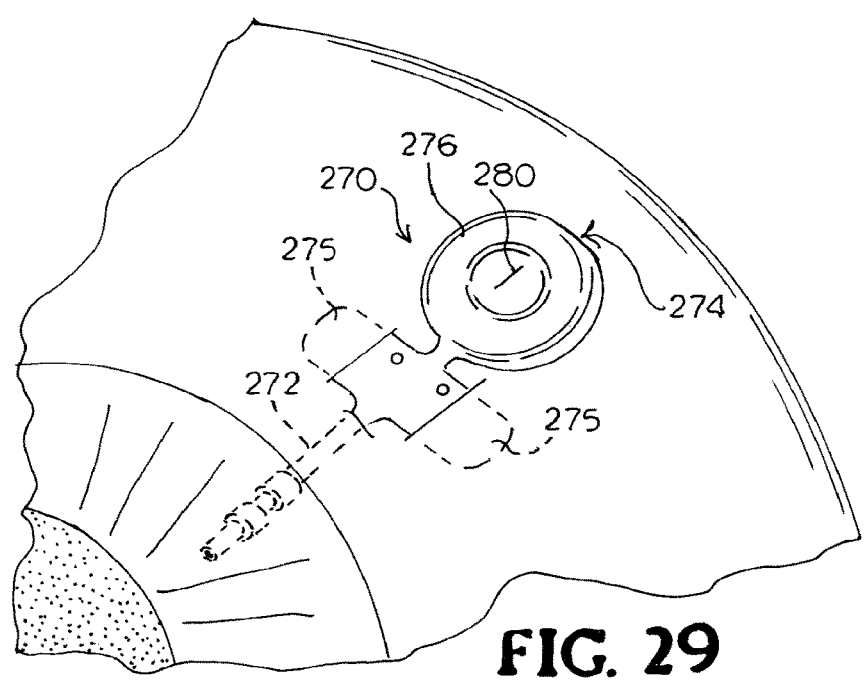
FIG. 29 is a perspective schematic view of the drainage device as shown in FIG. 27 implanted in an eye.
Figure 27:
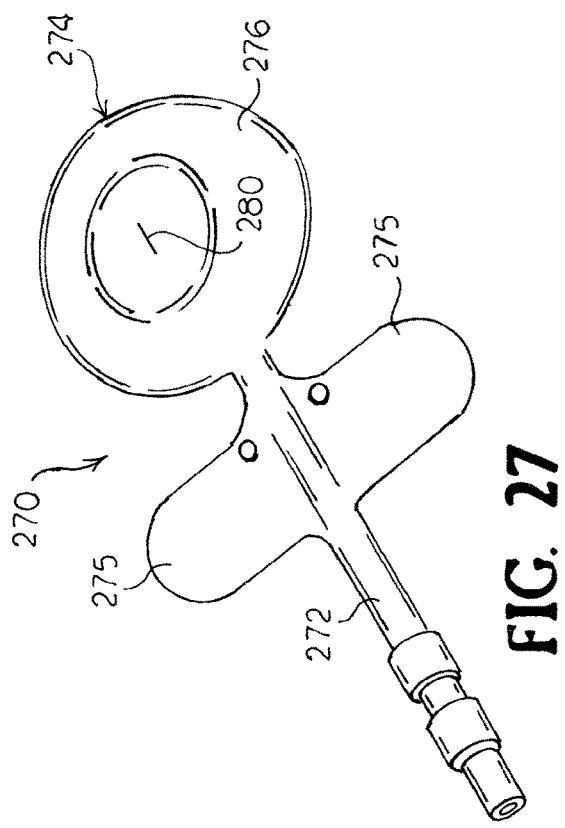
FIG. 27 is a perspective view of a eighth embodiment of a drainage device for reducing intraocular pressure.
Figure 28:
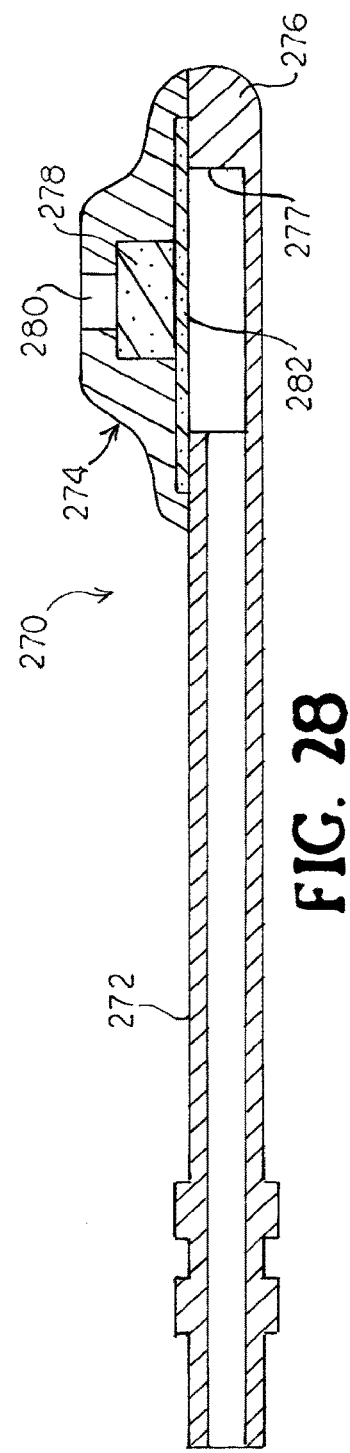
FIG. 28 is a longitudinal cross-section of the drainage device as shown in FIG. 27.

Referring now to FIGS. 27-29, an eighth embodiment of an implantable ocular drainage device is shown and generally designated at 270. The drainage device 270 comprises a tubular body 272 and an outlet assembly 274, the outlet assembly 274 including a generally circular head portion 276. A pair of opposed longitudinal suture wings 275 extend radially outwardly from the body 272 intermediate along the length of the body 272 between the head portion 276 and the distal end of the body 272.

Referring to FIG. 28, the head portion 276 defines an interior cavity 277 for accommodating a removable filter or cartridge 278. The head portion 276 has a slit valve 280 opening into the cavity. In this embodiment of the drainage device 270, a second permanent filter 282 is disposed in the head portion 276 upstream of the removable cartridge 278. At least a portion of the tubular body 272 of the drainage device 270 is implantable into the anterior chamber of an eye for draining aqueous humor. The permanent filter 282 functions to prevent infection during cartridge 278 replacement. The filter 252 is disposed within the head portion 245 and is sealed against the flange 249 such that the inlet 249 into the cavity is closed or substantially closed by the filter 252. As in other embodiments, the cartridge 278 may be formed from expandable material to ensure a fluid-tight seal with the head portion. The cartridge 278 may include agents to prevent bio-fouling and clogging of the permanent filter 282 from the external environment. Both filters 278, 282 function to prevent bacterial migration. In particular, the permanent filter 282 remains in place when the second filter 278 is removed during replacement. In this manner, the removable filter 278 may be selected based its ability to regulate intraocular pressure by providing a predetermined resistance to outflow of aqueous humor from the anterior chamber of the eye into the tear film. The valve 280 permits the outflow of aqueous humor that has passed through the filters 278, 282 to flow onto the sclera and enter the tear film while providing resistance to aqueous humor outflow and restriction against bacterial incursion. In this manner, the cartridge 278 may be used to fine tune the pressure in the eye non-invasively via replacement of the cartridge 278.

In addition to the materials already described, the body and the outlet assembly of the embodiments of drainage devices 30, 70, 100, 140, 170, 220, 240, 270 may be formed from materials having good biocompatibility and durability and which are sufficiently flexible. Suitable materials include a material selected from the group consisting of silicone, acrylic, polyimide, polypropylene, polymethyl methacrylate, polytetrafluoroethylene, hydrogels, polyolefin, polyolefin resins such as polyethylene, polyisobutylene, ethylene-vinyl acetate copolymer, polynorbornene, polyvinylchloride, polyester, polyvinyl alcohol, polyvinyl pyrolidone, polyethersulfone (PES), poly(styrene-isobutylstyrene), polysilicon, polyurethane, glass and ceramics such as alumina and titania, metals such as stainless steel, titanium, gold, silver, platinum or nitinol, collagen or chemically-treated collagen, hydroxyapetite, natural and synthetic rubbers such as polybutadiene, polyisoprene, SBR (Styrene Butadiene Rubber), and SIR, polyacetal resin, ABS (Acrylonitrile-Butadiene-Stylene) resin, solid HEMA polymer, and combinations thereof.

At least a portion of the filters 40, 80, 110, 150, 182, 252, 278 has a pore size that is sufficiently small to prevent ingress of microorganisms, such as bacteria, viruses, fungi and spores thereof, from entering the lumen 46 for minimizing the opportunity for reflux infection. A pore size of less than about 0.4 μm is sufficiently small to prevent ingress of microorganisms. In some embodiments, the filter 40, 80, 110, 150, 182, 252, 278 comprise a microporous/nanoporous membrane or polymer network, fiber network, or microcapsular material having a network of pores. Microporous filter membranes suitable for use with ophthalmic devices include micropore filter membranes (polycarbonate, polyethersulfone, polyvinylidene fluoride), porous hydrogels (polyacrylamide, alginate, polyhydroxyethylmethacrylate), and microperforated silicone or polyvinyl polymer, such as polyvinyl alcohol which is expandable within the lumen 46. Other suitable polymers include a polyolefin polymer, an ethylene-vinyl alcohol copolymer, a polyacrylonitrile polymer, a cellulose polymer, cellulose acetate polymer, and a polyamide polymer. Filter membrane nanotechnology may also be useful to fabricate microporous membranes to be biocompatible, non-degradable, and immunoisolating. Other materials, such as ceramics, polymers and metals, such as titanium, may also be suitable for the filter. The filters may be created using lithography or electrospinning.

The filter 40, 80, 110, 150, 182, 252, 278 may have an antibiotic coating to prevent contamination during replacement. Suitable coatings for the filter are described in co-pending U.S. Patent Application Publication No. 2010/0057055, the contents of which are hereby incorporated by reference in their entirety.

At least a portion of the external surfaces of the body, the tabs, and inner surface of the head portion of the drainage devices 30, 70, 100, 140, 170, 220, 240, 270 may be coated with a porous cellular ingrowth coating. The porous cellular ingrowth coating is coated on at least the portion of the drainage device 30, 70, 100, 140, 170, 220, 240, 270 that is in contact with the sclera and conjunctiva when the drainage device is implanted. The porous cellular ingrowth coating may be a hydroxyapatite or porous polyethylene that serves to promote cell adhesion. Selected growth factors may be adsorbed onto this coating to enhance cellular ingrowth. The coating is receptive to tissue attachment so that the body and the tabs, suture bars and suture wings of the drainage devices 30, 70, 100, 140, 170, 220, 240, 270 may be securely anchored in position. This feature enables the drainage devices 30, 70, 100, 140, 170, 220, 240, 270 to resist in situ motion and displacement. To further promote tissue ingrowth and cell attachment, the body of the drainage devices 30, 70, 100, 140, 170, 220, 240, 270 may include surface alterations, such as texturing, roughening or other patterned or non-patterned irregularities.

The remaining surfaces of the drainage devices 30, 70, 100, 140, 170, 220, 240, 270, including the entire lumenal surface, the portions of the external surface of the drainage device not in contact with the sclera, and the filter surfaces, may be coated with a bio-inert surface coating to enhance surface biocompatibility. Such coatings may include bio-inert polymer coatings such as phosphoryl choline (PC) and polyethylene oxide (PEO). Both PC and PEO polymer coatings down regulate deleterious biological reactions, primarily by attracting a large and stable hydration shell when grafted onto a surface. Bio-inert surface coatings may be further modified with biologically active molecules such as heparin, spermine, surfactants, proteases or other enzymes, or other biocompatible chemicals amendable to surface immobilization. PEO also is amendable to end-group coupling for surface immobilization of the biologically active molecules. The addition of such bioactive molecules could advantageously impart specific desired functionality, for example, allowing a further increase in the hydrophilicity of the surface.

The coating for the drainage devices 30, 70, 100, 140, 170, 220, 240, 270 can also comprise material that includes a therapeutic agent as well as antifibrotic and antimicrobial agents. The therapeutic agent can be selected from the group consisting of heparin, selenium, TGF-beta, an intraocular pressure-lowering drug, and an anti-proliferative agent. The coatings can be, for example, a drug eluting coating, an antithrombogenic coating, and a lubricious coating. Materials that may be used for a drug-eluting coating include parylene C, poly(butyl methacrylate), poly(methyl methacrylate), polyethylene-co-vinyl acetate, and other materials known in the art. In addition, these agents may incorporated into the filter material via covalent, metallic, ionic, or non-covalent bonding.

All embodiments of the drainage device 30, 70, 100, 140, 170, 220, 240, 270 described herein may be surgically implanted under topical anesthesia, possibly supplemented subconjunctivally. In general, the drainage device 30, 70, 100, 140, 170, 220, 240, 270 may be inserted into the sclera using routine operative procedures.

Referring to FIGS. 4 and 5 with respect to the first embodiment of the drainage device 30, the procedure for implanting the drainage device 30 includes the initial step of dissecting or piercing the conjunctiva into Tenon's space about 4 mm from the limbus in the fornix space. The distal end 44 of the tube 32 is then threaded through the incision in the fornix so that the body 32 passes under the conjunctiva and the outlet assembly 34 lies externally on the conjunctiva in the cul-de-sac region underneath the eyelid.

The conjunctiva is then dissected down from the fornix incision to the limbus to expose the underlying sclera for insertion of the distal end 44 of the tube 32. A needle, trocar, scalpel, or any of a multitude of instruments familiar to ophthalmologic practitioners may be used at the site of the now exposed sclera to make a stab incision through the sclera into the anterior chamber. The pointed tip at the distal end 44 of the body 32 is then inserted through the scleral tract of the incision and into the anterior chamber or posterior chamber of the eye. The remainder of the body 32 remains positioned external to the ocular surface of the eye. Optionally, the body 32 may be sutured to the sclera.

Next, two parallel cuts are made into the conjunctiva adjacent the outlet assembly 34 approximately 2 mm to 4 mm apart. A tab 54 is inserted into each cut. The tabs 54 may be sutured to the sclera with a 10-0 nylon suture. A suture is then used to close the conjunctiva around the tabs 54 while leaving the intermediate portion of the outlet assembly 34 exposed. In some embodiments, holes may be provided in the tabs for additional sutures into the sclera, providing further stability to the drainage device 30 until the biointegration is complete. Similarly, for embodiments of the drainage device 70, 150, 170 including suture bars 94 162 or suture wings 202, the suture bars 94, 162 or suture wings 202 are sutured into the sclera for securing the body of the device. The conjunctiva is then restored and the incision is closed with a suture using a known method or a biologically acceptable adhesive. For drainage devices 100, 220, 240, 270 with lips or rims or a conduit, a purse-string 8-0 suture may be used to close the conjunctiva tightly around the outlet.

In use, aqueous humor flows into the drainage device 30 from the anterior chamber or posterior chamber of the eye and passes through the body 32 via the lumen 46 and through the filter 40 and drains via the slit valve 38 in the outlet assembly 34. As described above, the flow path through the drainage device 30 can be configured for regulating drainage of aqueous humor at a predetermined rate and further for resisting the incursion of microorganisms. The outflow of aqueous humor is consistently regulated by the filter 40 and valve 38, either separately or in combination, so that a predictable outflow rate can be calculated for proper drainage for maintaining intraocular pressure of about 6 mmHg to about 18 mmHg. The flow rate will range based on aqueous humor production, which is usually between about 1 uL/min and about 4 uL/min, while avoiding hypotony at less than about 5 mmHg. The dual filter-valve mechanism provides a physiologic design to control pressure in the eye. The valve functions as an episcleral venous pressure device to provide a lower pressure limit. The filter provides resistance in the manner of the trabecular meshwork in a human eye. The combination provides a natural pressure change based on diurnal changes in aqueous humor production and ocular pulse. Thus, the embodiments of the drainage device 30, 70, 100, 140, 170, 220, 240, 270 described herein effectively provide outflow characteristics which model the aqueous humor dynamics of a healthy eye.

The filter 40, 80, 110, 150, 182, 252, 278 can be replaced if there is deterioration or damage over the course of using the drainage device as the protein or other substances contained in the aqueous humor clog the filter. The slit valves or removable caps permit access to the filter 40, 80, 110, 150, 182, 252, 278 so that the filter can be removed and replaced. Accordingly, the filter 40, 80, 110, 150, 182, 252, 278 can be replaced with a new replacement filter by removing the old filter and inserting a new filter via the slit valve or caps. In this way, the intraocular pressure relieving effect of the drainage devices 30, 70, 100, 140, 170, 220, 240, 270 can be sustained for extended periods of time. Because only the filter is replaced, the cost of replacement is much cheaper than the case where the drainage device needs to be re-installed entirely.

In another embodiment, the head portion of the drainage device 30, 70, 100, 140, 170, 220, 240, 270 may be provided with an access port (not shown) so that access to the filter would be available without disrupting the position of the head portion. The access port could, in certain embodiments, be integrated with the slit valve. Other arrangements may be readily envisioned by those skilled in the art.

The embodiments of the drainage device 30, 70, 100, 140, 170, 220, 240, 270 described herein may comprise any of the materials previously described above. The drainage device 30, 70, 100, 140, 170, 220, 240, 270 can be fabricated through conventional micro machining techniques or through procedures commonly used for fabricating optical fibers. For example, in some embodiments, the drainage devices 30, 70, 100, 140, 170, 220, 240, 270 are drawn with a bore, or lumen, extending therethrough. In some embodiments, the tapered tip at the distal end of the body can be constructed by shearing off an end of the tubular body. This can create the tapered portion that can be used to puncture or incise the eye tissue during implantation and dilate the puncture or incision during advancement of the drainage device 30, 70, 100, 140, 170, 220, 240, 270. Other methods of manufacturing the drainage device 30 can be used.

Each of the embodiments of the drainage device 30, 70, 100, 140, 170, 220, 240, 270 provides a method for treating glaucoma wherein aqueous humor is permitted to flow out of an anterior chamber or posterior chamber of the eye through a surgically implanted pathway to an external ocular surface. The drainage device 30, 70, 100, 140, 170, 220, 240, 270 is implanted with minimal invasiveness of the ocular tissue and minimal sense of a foreign object. Immobilizing the outlet assembly of the drainage device 30, 70, 100, 140, 170, 220, 240, 270 is an important feature. Immobilization is enhanced by using a biocompatible material and providing the portions of the drainage device 30, 70, 100, 140, 170, 220, 240, 270 in contact with eye tissue with the porous cellular ingrowth surface to promote tissue integration to the sclera. Coating the surface of the drainage device 30, 70, 100, 140, 170, 220, 240, 270 with polymers or biologically active molecules or providing active agents within the polymers also promotes surface biocompatibility or immobilization post-implantation. All of these features contribute to minimizing problems caused by eye movement (micromotion), including a feeling of invasiveness to the ocular tissues, pain, and displacement of the drainage device 30, 70, 100, 140, 170, 220, 240, 270. Eliminating micromotion prevent adverse events such as fibrosis, erosion, exposure, and/or extrusion.

In addition, the embodiments of the drainage device 30, 70, 100, 140, 170, 220, 240, 270 as described herein can be used to treat other ocular disorders in addition to glaucoma. In one embodiment, the drainage device 30, 70, 100, 140, 170, 220, 240, 270 is used to treat dry eye, wherein the aqueous humor exiting the drainage device combines with the tear film for enhancing moisture and lubrication in the eye.

Although the present device has been shown and described in considerable detail with respect to only a few exemplary embodiments thereof, it should be understood by those skilled in the art that we do not intend to limit the device to the embodiments since various modifications, omissions and additions may be made to the disclosed embodiments without materially departing from the novel teachings and advantages of the device, particularly in light of the foregoing teachings. Accordingly, we intend to cover all such modifications, omission, additions and equivalents as may be included within the spirit and scope of the device as defined by the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

We claim:

1. An apparatus for draining aqueous humor from an eye for reducing intraocular pressure, the apparatus comprising:
    a tube extending between an inlet end and an outlet end, the tube defining a passage for a fluid to flow from the inlet end to the outlet end;
    a housing defining a cavity in fluid communication with the outlet end of the tube, the cavity configured to receive the fluid from the tube, the housing including an opening configured to allow the fluid to flow out from the cavity to an external area; and
    a filtration element disposed in at least one of the tube or the housing, the filtration element having a length extending from a distal end and a proximal end, the distal end being positioned closer to the inlet end of the tube, the filtration element including a plurality of pores having a plurality of respective pore sizes, the plurality of pores being arranged in the filtration element in order of decreasing size from the distal end to the proximal end,
    wherein the fluid flows through the tube and the housing via the plurality of pores from the distal end to the proximal end of the filtration element, and the plurality of pores provide a predetermined resistance to the flow of the fluid.

2. The apparatus of claim 1, wherein the filtration element includes a predetermined resistance provided by the plurality of pores depends on the length of the resistive component.

3. The apparatus of claim 1, wherein the plurality of pores includes pores having a diameter less than or equal to about 0.4 μm.

4. The apparatus of claim 1, wherein the filtration element is removable or installable via the opening of the housing.

5. The apparatus of claim 1, further comprising an outer sheath disposed over the filtration element.

6. The apparatus of claim 5, wherein the outer sheath is a hollow mesh cage.

7. The apparatus of claim 5, wherein the resistive component and the outer sheath are expandable to form a seal with at least one of the tube or the housing.

* * * * *